United States Patent [19]

Bowles et al.

[11] Patent Number: 5,563,151
[45] Date of Patent: Oct. 8, 1996

[54] AMINO ACID DERIVATIVES AS PAF-RECEPTOR ANTAGONISTS

[75] Inventors: Stephen A. Bowles; Andrew Miller; Mark Whittaker, all of Oxford, United Kingdom

[73] Assignee: British Biotech Pharmaceuticals limited, Oxford, United Kingdom

[21] Appl. No.: 256,140

[22] PCT Filed: Jan. 6, 1993

[86] PCT No.: PCT/GB93/00009

§ 371 Date: Sep. 1, 1994

§ 102(e) Date: Sep. 1, 1994

[87] PCT Pub. No.: WO93/14072

PCT Pub. Date: Jul. 19, 1993

[30] Foreign Application Priority Data

Jan. 7, 1992 [GB] United Kingdom .................. 9200245

[51] Int. Cl.⁶ ...................... C07D 471/04; A61K 31/435
[52] U.S. Cl. ...................... 514/303; 546/118; 546/336; 546/300; 548/307.1; 548/309.7; 548/306.4
[58] Field of Search ............................ 546/118; 514/303

[56] References Cited

U.S. PATENT DOCUMENTS

| | | | |
|---|---|---|---|
| 4,288,536 | 9/1981 | Goettert et al. | 430/619 |
| 4,610,983 | 9/1986 | Takagawa et al. | 514/230 |
| 5,071,837 | 12/1991 | Doherty et al. | 514/18 |
| 5,158,866 | 10/1992 | Simpson et al. | 430/617 |
| 5,215,968 | 6/1993 | Nickel et al. | 514/19 |

FOREIGN PATENT DOCUMENTS

| | | | |
|---|---|---|---|
| 9100725 | 1/1991 | WIPO | A61K 37/00 |
| 9116313 | 10/1991 | WIPO | C07D 235/04 |

OTHER PUBLICATIONS

Lauf, P. W. *Research Disclosure* 29963 (Mar. 1989).

*Primary Examiner*—Cecilia Tsang
*Assistant Examiner*—King L. Wong
*Attorney, Agent, or Firm*—Hale and Dorr

[57] ABSTRACT

Compounds of general formula I:

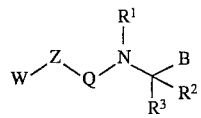

wherein W represents imidazo [4,5-c]pyridin-1-yl, imidazo [4,5-c]pyridin-3-yl and imidazo [4,5-c]pyridin-5-yl optionally substituted with one or more —$C_1$–$C_6$ alkyl substituents; Z represents a) a divalent alkanediyl, alkenediyl or alkynediyl group; b) a —$(CH_2)_q U(CH_2)_r$— group, optionally substituted, wherein q is an integer from 0–3, r is an integer from 0–3 and U is —O— or —S—; Q represents a carbonyl, thiocarbonyl or sulphonyl group; B represents a) a —$VR^8$ group wherein V is —C(=O)O— or —$CH_2$O—; are antagonists of platelet activating factor (PAF).

10 Claims, No Drawings

AMINO ACID DERIVATIVES AS PAF-RECEPTOR ANTAGONISTS

This invention relates primarily to novel substituted amino acid derivatives that possess pharmaceutical activity as antagonists of PAF.

Platelet activating factor (PAF) is a bioactive phospholipid which has been identified as 1-O-hexadecyl/octadecyl-2-acetyl-sn-glyceryl-3-phosphoryl choline. PAF is released directly from cell membranes and mediates a range of potent and specific effects on target cells resulting in a variety of physiological responses which include hypotension, thrombocytopenia, bronchoconstriction, circulatory shock, and increased vascular permeability (oedema/erythema). It is known that these physiological effects occur in many inflammatory and allergic diseases and PAF has been found to be involved in a number of such disorders including asthma, endotoxin shock, adult respiratory distress syndrome, glomerulonephritis, immune regulation, transplant rejection, gastric ulceration, psoriasis, and cerebral, myocardial and renal ischemia. Thus the compounds of the invention, by virtue of their ability to antagonise the actions of PAF, should be of value in the treatment of any of the above conditions and any other conditions in which PAF is implicated (e.g. embryo implantation).

Compounds that have been disclosed as possessing activity as PAF antagonists include compounds which are structurally related to the PAF molecule such as glycerol derivatives (EP-A-0238202), and heterocyclic compounds such as 5-oxy derivatives of tetrahydrofuran (U.S. Pat. No. 4,888,337) and 2,5-diaryl tetrahydrofurans (EP-A-0144804). Recently a more potent 2,5-diaryl tetrahydrofuran derivative, (trans)-2-(3-methoxy-5-methylsulphonyl-4-propoxyphenyl)- 5-(3,4,5-trimethoxyphenyl)tetrahydrofuran (L-659,989) has been disclosed (EP-A-0199324). In our International patent application no. WO 91/17157 we disclose a series of γ-butyrolactol derivatives as PAF antagonists. The compounds of WO 91/17157 differ from the 5-oxy derivatives of tetrahydofuran described in U.S. Pat. No. 4,888,337 and from the 2,5-diaryl tetrahydrofurans such as L-659,989, in that they feature an appended heterocycle with an unsubstituted sp² nitrogen atom. There are a number of other PAF antagonists, in addition to those of WO 91/17157, for which the presence of a heterocyclic sp² nitrogen atom appears to be an important requirement for activity (Whittaker, M., Curr. Opin. Thera. Patents 2(5), 583–623 (1992)).

For the compounds of the present invention the presence of a heterocyclic group possessing an unsubstituted sp² nitrogen atom is also a requirement for PAF antagonist activity. However, the compounds of the present invention differ from the other PAF antagonists refered to above in that they are amino acid derivatives.

The present invention provides novel and useful substituted amino acid derivatives and their pharmaceutically acceptable acid addition salts, and pharmaceutical uses thereof as PAF antagonists.

According to a first aspect of the invention there is provided a compound of general formula I:

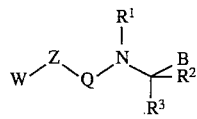

wherein:

W represents pyrid-3-yl, benzimidazol-1-yl, imidazo[4,5-c]pyridin-1-yl, imidazo[4,5-c]pyridin-3-yl and imidazo[4,5-c]pyridin-5-yl optionally substituted with one or more —$C_1$–$C_6$ alkyl substituents;

Z represents:

a) a divalent alkanediyl, alkenediyl or alkynediyl group from 2 to 12 carbon atoms which may be a straight or branched-chain provided that, when Z represents a branched chain at least two carbon atoms separate W from the group Q, wherein the said group is either unsubstituted or substituted by one or more substituents selected from hydroxy, —$OC_1$–$C_6$ alkyl, —$SC_1$–$C_6$ alkyl and halo; or b) a —$(CH_2)_qU(CH_2)_r$— group, optionally substituted by one or more substituents selected from hydroxy, —$OC_1$–$C_6$ alkyl, halo and nitrile, wherein q is an integer from 0–3, r is an integer from 0–3 and U is —O—, —S— or a furandiyl, tetrahydrofurandiyl, thiophenediyl, tetrahydrothiophenediyl, thiazolediyl, tetrahydrothiazolediyl, piperazinediyl, piperidinediyl, cyclopentanediyl, cyclohexanediyl, cycloheptenediyl or benzenediyl group (provided that, when U is a 1,4-benzenediyl group q is not an integer of 1); or c) a

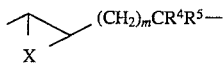

group wherein m is an integer from 0–3, X is —O—, —S— or —$CH_2$— and each of $R^4$ and $R^5$ is independently hydrogen or —$C_1$–$C_6$ alkyl;

Q represents a carbonyl, thiocarbonyl or sulphonyl group or a bond $R^1$ represents hydrogen, —$C_1$–$C_6$ alkyl, —$C_2$–$C_6$ alkenyl, —$C_2$–$C_6$ alkynyl, —$COC_1$–$C_6$ alkyl, —$CO_2C_1$–$C_6$ alkyl, —($CO_2C_1$–$C_6$ alkyl)phenyl, —($C_1$–$C_6$ alkyl)$CO_2C_1$–$C_6$ alkyl, —($C_1$–$C_6$ alkyl)phenyl, —$C_3$–$C_8$ cycloalkyl, —$C_4$–$C_8$ cycloalkenyl or phenyl optionally substituted by one or more substituents selected from —$C_1$–$C_6$ alkyl, —$OC_1$–$C_6$ alkyl, halogen, —$CF_3$ and —CN;

$R^2$ represents hydrogen, halogen, —$C_1$–$C_6$ alkyl optionally substituted by one or more halogen atoms, $C_2$–$C_6$ alkenyl, $C_2$–$C_6$ alkynyl, —($C_1$–$C_6$ alkyl)$CO_2C_1$–$C_6$ alkyl, —($C_1$–$C_6$ alkyl)$SC_1$–$C_6$ alkyl, —($C_1$–$C_6$ alkyl)$OC_1$–$C_6$ alkyl, —($C_1$–$C_6$ alkyl)N($C_1$–$C_6$ alkyl)$_2$, —$C_3$–$C_8$ cycloalkyl, —$C_4$–$C_8$ cycloalkenyl, —($C_1$–$C_6$ alkyl)$C_3$–$C_8$ cycloalkyl, —($C_1$–$C_6$ alkyl)$C_4$–$C_8$ cycloalkenyl, —($C_1$–$C_6$ alkyl)$OC_3$–$C_8$ cycloalkyl, —($C_1$–$C_6$ alkyl)$OC_4$–$C_8$ cycloalkenyl, —($C_1$–$C_6$ alkyl)$SC_3$–$C_8$ cycloalkyl, —($C_1$–$C_6$ alkyl)$SC_4$–$C_8$ cycloalkenyl, a side chain of a naturally occurring amino acid, a group —D or —($C_1$–$C_6$ alkyl)OD wherein D is a group

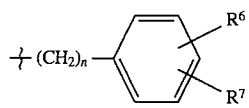

wherein n is an integer from 0 to 3, and
each of $R^6$ and $R^7$ is independently hydrogen, —$C_1$–$C_6$ alkyl, —$C_2$–$C_6$ alkenyl, —$C_2$–$C_6$ alkynyl, halogen, —CN, —$CO_2H$, —$CO_2C_1$–$C_6$ alkyl, —$CONH_2$, —$CONHC_1$–$C_6$ alkyl, —$CON(C_1$–$C_6$ alkyl)$_2$, —CHO, —$CH_2OH$, —$CF_3$, —$OC_1$–$C_6$ alkyl, —$SC_1$–$C_6$ alkyl, —$SOC_1$–$C_6$ alkyl, —$SO_2C_1$–$C_6$ alkyl, —$NH_2$ or —NHCOMe; or $R^1$ together with $R^2$ and the atoms to which they are attached form a 5 to 8 membered nitrogen-containing heterocyclic ring;

$R^3$ represents hydrogen or halogen;

B represents:

a) a —$VR^8$ group wherein V is —C(═O)—, —C(═O)O—, —$CH_2O$—, —$CH_2OC$(═O)—,

—C(=S)—, —CH$_2$OC(=O)NH—, —C(=S)O—, —CH$_2$S—, —C(=O)NHSO$_2$— or —SO$_2$NHC(=O)—; and R$^8$ is hydrogen, —C$_1$–C$_{18}$ alkyl, —C$_2$–C$_{18}$ alkenyl, —C$_2$–C$_{18}$ alkynyl, —(C$_1$–C$_6$ alkyl)OC$_1$–C$_6$ alkyl, —(C$_1$–C$_6$ alkyl)SC$_1$–C$_6$ alkyl, —(C$_1$–C$_6$ alkyl)O(C$_1$–C$_6$ alkyl)OC$_1$–C$_6$ alkyl, —C$_3$–C$_8$ cycloalkyl, —C$_4$–C$_8$ cycloalkenyl or pyridyl, (any of which may optionally be substituted with one or more substituents selected from halogen, hydroxyl, nitro, nitrile or carboxyl), —C$_1$–C$_4$ perfluoroalkyl, a group —D as defined above or a —(C$_1$–C$_6$ alkyl)OD group wherein D is as defined above;

b) a —CH$_2$NR$^9$R$^{10}$ group or a —CONR$^9$R$^{10}$ group wherein each of R$^9$ and R$^{10}$ is independently hydrogen, —C$_1$–C$_{18}$ alkyl, —C$_2$–C$_{18}$ alkenyl, —C$_2$–C$_{18}$ alkynyl, —C$_3$–C$_8$ cycloalkyl, —C$_4$–C$_8$ cycloalkenyl, pyridyl (any of which may optionally be substituted with one or more substituents selected from halogen, hydroxyl, nitro, nitrile or carboxyl) or a group —D as defined above or R$^9$ and R$^{10}$ together with the nitrogen atom to which they are attached form a 5 to 8 membered nitrogen-containing heterocyclic ring;

c) a group Y where Y is a 5- or 6-membered heterocyclic ring containing one or more heteroatoms selected from nitrogen, oxygen and sulphur and the ring may be optionally substituted with one or more substituents selected from —C$_1$–C$_6$ alkyl, —OC$_1$–C$_6$ alkoxy, halogen, —CF$_3$ and —CN; or d) a group —CH$_2$—Y or C(=O)NHY; where Y is as defined above;

or a pharmaceutically or veterinarily acceptable acid addition salt or hydrate thereof.

Hereafter in this specification the term "compound" includes "salt" or "hydrate" unless the context requires otherwise.

As used herein the term "halogen" or its abbreviation "halo" means fluoro, chloro, bromo or iodo.

As used herein the term "C$_1$–C$_6$ alkyl" refers to straight chain or branched chain hydrocarbon groups having from one to six carbon atoms. Illustrative of such alkyl groups are methyl, ethyl, propyl, isopropyl, butyl, isobutyl, sec-butyl, tert-butyl, pentyl, neopentyl and hexyl.

As used herein the term "C$_1$–C$_{18}$ alkyl" refers to straight chain or branched chain hydrocarbon groups having from one to eighteen carbon atoms. Illustrative of such alkyl groups are methyl, ethyl, propyl, isopropyl, butyl, isobutyl, sec-butyl, tert-butyl, pentyl, neopentyl, hexyl, decyl, dodecyl, tridecyl, tetradecyl, pentadecyl, hexadecyl, heptadecyl and octadecyl. From one to six carbon atoms may be preferred.

As used herein the term "C$_2$–C$_6$ alkenyl" refers to straight chain or branched chain hydrocarbon groups having from two to six carbon atoms and having in addition one double bond, of either E or Z stereochemistry where applicable. This term would include for example, vinyl, 1-propenyl, 1- and 2-butenyl and 2-methyl- 2-propenyl.

As used herein the term "C$_2$–C$_{18}$ alkenyl" refers to straight chain or branched chain hydrocarbon groups having from two to eighteen carbon atoms and having in addition one or more double bonds, of either E or Z stereochemistry where applicable. This term would include for example, vinyl, 1-propenyl, 1- and 2-butenyl, 2-methyl-2-propenyl, geranyl, and farnesyl. From two to six carbon atoms may be preferred.

As used herein the term "C$_2$–C$_6$ alkynyl" refers to straight chain or branched chain hydrocarbon groups having from two to six carbon atoms and having in addition one triple bond. This term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

As used herein the term "C$_2$–C$_{18}$ alkynyl" refers to straight chain or branched chain hydrocarbon groups having from two to six carbon atoms and having in addition one triple bond. This term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl, 5-hexynyl, 10-undecynyl, 4-ethyl-1-octyn- 3-yl, 7-dodecynyl, 9-dodecynyl, 10-dodecynyl, 3-methyl-1-dodecyn-3-yl, 2-tridecynyl, 11-tridecynyl, 3-tetradecynyl, 7-hexadecynyl and 3-octadecynyl. From two to six carbon atoms may be preferred.

As used herein, the term "C$_1$–C$_4$ perfluoroalkyl" refers to straight chain or branched chain groups having from one to four carbon atoms and substituted by more than one fluorine atom. This term would include, for example, trifluoromethyl, 2,2,2-trifluoroethyl, pentafluoroethyl, 3,3,3-trifluoro-n-propyl, sexafluoro-i-propyl, septafluoro-n-propyl, septafluoro-i-propyl, 4,4,4-trifluoro-n-butyl, nonafluoro-n-butyl, nonafluoro-sec-butyl and nonafluoro-i-butyl.

As used herein the term "OC$_1$–C$_6$ alkyl" refers to straight chain or branched chain alkoxy groups having from one to six carbon atoms. Illustrative of such alkoxy groups are methoxy, ethoxy, propoxy, isopropoxy, butoxy, isobutoxy, sec-butoxy, tert-butoxy, pentoxy, neopentoxy and hexoxy.

As used herein the term "SC$_1$–C$_6$ alkyl" refers to straight chain or branched chain alkylthio groups having from one to six carbon atoms. Illustrative of such alkyl groups are methylthio, ethylthio, propylthio, isopropylthio, butylthio, isobutylthio, sec-butylthio, tert-butylthio, pentylthio, neopentylthio and hexylthio.

As used herein, the term "C$_3$–C$_8$ cycloalkyl" refers to an alicyclic group having from 3 to 8 carbon atoms. Illustrative of such cycloalkyl groups are cyclopropyl, cyclobutyl, cyclopentyl and cyclohexyl.

As used herein, the term "C$_4$–C$_8$ cycloalkenyl" refers to an alicyclic group having from 4 to 8 carbon atoms and having in addition one or more double bonds. Illustrative of such cycloalkenyl groups are cyclopentenyl, cyclohexenyl, cycloheptenyl and cyclooctenyl.

As used herein, the term "side chain of a naturally occurring amino acid" includes the side chains of alanine, arginine, asparagine, aspartic acid, cysteine, cystine, glutamic acid, glycine, histidine, 5-hydroxylysine, 4-hydroxyproline, isoleucine, leucine, lysine, methionine, phenylalanine, proline, serine, threonine, tryptophan, tyrosine, valine, α-aminoadipic acid, α-amino-n-butyric acid, 3,4-dihydroxyphenylalanine, homoserine, α-methylserine, ornithine, pipecolic acid, and thyroxine. The amino acid side chains may be protected; for example the carboxyl groups of aspartic acid, glutamic acid and α-aminoadipic acid may be esterified (for example as a C$_1$–C$_6$ alkyl ester), the amino groups of lysine, ornithine, 5-hydroxylysine, 4-hydroxyproline may be converted to amides (for example as a COC$_1$–C$_6$ alkyl amide) or carbamates (for example as a C(=O)OC$_1$–C$_6$ alkyl or C(=O)OCH$_2$Ph carbamate), the hydroxyl groups of 5-hydroxylysine, 4-hydroxyproline, serine, threonine, tyrosine, 3,4-dihydroxyphenylalanine, homoserine, α-methylserine and thyroxine may be converted to ethers (for example a C$_1$–C$_6$ alkyl or a (C$_1$–C$_6$ alkyl)phenyl ether) or esters (for example a C(=O)C$_1$–C$_6$ alkyl ester) and the thiol group of cysteine may be converted to thioethers (for example a C$_1$–C$_6$ alkyl thioether) or thioesters (for example a C(=O)C$_1$–C$_6$ alkyl thioester). The stereochemistry at the carbon atom to which the amino acid side chain is attached may be either D or L.

As used herein, the term "nitrogen-containing heterocyclic ring" refers to an aromatic or alicyclic ring comprising one or more nitrogen atoms and optionally one or more other heteroatoms. Illustrative of such rings are pyrrolidine, piperidine, hexamethyleneimine, heptamethylenimine, morpholine and piperazine.

In compounds of this invention, the presence of several asymmetric carbon atoms gives rise to diastereoisomers, each of which consists of two enantiomers, with the appropriate R or S stereochemistry at each chiral center. The invention is understood to include all such diastereoisomers, their optically active enantiomers and mixtures thereof.

The term "pharmaceutically or veterinarily acceptable acid addition salt" refers to a salt prepared by contacting a compound of formula (I) with an acid whose anion is generally considered suitable for human or animal consumption.

Examples of pharmaceutically and/or veterinarily acceptable acid addition salts include the hydrochloride, sulphate, phosphate, acetate, propionate, lactate, maleate, succinate and tartrate salts.

It is considered that the main structural features of compounds of general formula I that are particularly significant in providing their PAF antagonist activity, are the $sp^2$ nitrogen heterocycle (W group) and the subunit (i)

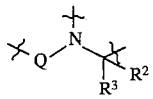

(i)

The linkage —Z— is considered to function as a spacer element, separating the $sp^2$ nitrogen heterocycle from the amino acid subunit. The nature or identity of the linkeage —Z— is therefore not thought to be particularly critical and any of the wide range of —Z— groupings specified above may be used with retention of PAF antagonist activity. Likewise, since the presence of the subunit (i) appears to be crucial for retention of PAF antagonist activity. There may be considerable variation of the substituent groups $R^1$, and B with out loss of such activity. Any of the the wide range of substituents $R^1$ and B defined above may be used with retention of PAF antagonist activity.

Of the $sp^2$ nitrogen heterocycles present in compounds described in our previous patent applications (WO 90/09997, WO 91/17157, WO 92/03422 and WO 92/03423) it is considered that those which are particularly prefered elements of the compounds of this invention are those specified above in relation to general formula I. However, it is expected that PAF antagonist activity may be found in compounds analogous to those of general formula I above, wherein W is a different $sp^2$ nitrogen heterocycle. The variety of $sp^2$ nitrogen heterocycles that could provide PAF antagonist activity include those disclosed in our patent application WO 91/17157 and those recently described by Whittaker (Whittaker, M., Curr. Opin. Thera. Patents 2(5), 583–623 (1992)) and Cooper (Cooper, K., et at., J. Med. Chem. 35(17), 3115–3129 (1992)). The exact nature of the interaction of the $sp^2$ nitrogen heterocycle and the receptor has not been determined, but it would appear that it is important for the heterocycle to possess at least one unsubstituted $sp^2$ nitrogen atom within the heterocyclic ring.

Preferred compounds include those in which, independently or in any compatible combination;

W represents pyrid-3-yl, 2-methylbenzimidazol-1-yl, 2-methylimidazo[4,5-c]pyridin-1-yl, 2-methylimidazo[4,5-c]pyridin-3-yl, imidazo[4,5-c]pyridin-5-yl and 2-methylimidazo[4,5-c]pyridin-5-yl;

Z represents a) an alkanediyl having from 3 to 11 carbon atoms (for example propylene, 2-hydroxypropylene, 1-methylpropylene, 1,1-dimethylpropylene, butylene, 1-methylbutylene, 1,1-dimethylbutylene, 3-hydroxybutylene, pentylene, 1-methylpentylene, 1,1-dimethylpentylene, 4-hydroxypenylene, 4-methoxypentylene, hexylene, 1,1-dimethylhexylene, heptylene, 1-methylheptylene, 1,1-dimethylheptylene, octylene, 1,1-dimethyloctylene, nonylene, decylene, undecylene) group, an alkenediyl (for example prop-2-enylene, pent-3-enylene hex-5-enylene) group or an alkynediyl (for example prop-2-ynylene, 1-methylprop-2-ynylene, but-3-ynylene, pent-4-ynylene and hex-5-ynylene) group, or;

b) a —$(CH_2)_qU(CH_2)_r$— group, optionally substituted by nitrile, wherein;

U represents —O—, —S— or a tetrahydrofurandiyl, furandiyl, a thiophenediyl, a piperidinediyl, a piperazinediyl or a benzenediyl group;

q represents an integer of 0, 1, or 2 (provided that, when U is a 1,4-benzenediyl group q is not an integer of 1);

r represents an integer of 0;

$R^1$ represents a hydrogen atom, a —$C_1$–$C_6$ alkyl (for example methyl, ethyl) group, a —$C_2$–$C_6$ alkenyl (for example allyl) group, a —$CO_2C_1$–$C_6$ alkyl (for example ethoxycarbonyl) group or a —$(C_1$–$C_6$ alkyl)$CO_2C_1$–$C_6$ alkyl (for example a ethoxycarbonylmethyl or a t-butyloxycarbonylmethyl) group;

$R^2$ represents a —$C_1$–$C_6$ alkyl (for example methyl, isopropyl, n-butyl, isobutyl or 2-methylpropyl) group, a —$C_2$–$C_6$ alkenyl (for example allyl) group, a —$(C_1$–$C_6$ alkyl)$SC_1$–$C_6$ alkyl (for example methylthioethylene) group, the side chain of a naturally occurring amino acid (for example the side chain of tryptophan), a group —D or a —$(C_1$–$C_6$ alkyl)OD group;

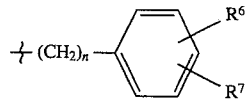

D n represents an integer of 0 or 1;

$R^6$ represents a hydrogen atom or a —$OC_1$–$C_6$ alkyl (for example methoxy) group;

$R^7$ represents a hydrogen atom;

$R^3$ represents a hydrogen atom;

when $R^2$ represents the side chain of a naturally occurring amino acid, particularly leucine, wherein the stereochemistry of the carbon atom to which $R^2$ and $R^3$ are attached is the same as, or the opposite to, that of the naturally occurring amino acid;

B represents a —$VR^8$ group, a —$CONR^9R^{10}$ group or a group Y wherein:

V represents a —C(=O)O— group, a —$CH_2OC(=O)$— group, a —$CH_2O$— group, a —$CH_2OC(=O)$— group or a —$CH_2OC(=O)NH$— group;

$R^8$ represents a hydrogen atom, —$C_1$–$C_{18}$ alkyl (for example methyl, ethyl, n-propyl, i-propyl, n-butyl, pentyl, hexyl, octyl, decyl, dodecyl, pentadecyl, hexadecyl, heptadecyl and octadecyl) group, a —$C_2$–$C_{18}$ alkenyl group (for example allyl), a —$(C_1$–$C_6$ alkyl)O$(C_1$–$C_6$ alkyl)O$C_1$–$C_6$ alkyl (for example a 2-( 2-ethoxyethoxy)ethyl) group, a pyridyl (for example a 2-pyridyl) group, a group D or a —$(C_1$–$C_6$ alkyl)OD group;

$R^9$ is a pyridyl (for example 2-pyridyl) group;

$R^{10}$ is a hydrogen atom;

Y is a pyrazinyl (for example 2-pyrazinyl) group or a oxadiazolyl (for example a 1,2,4-oxadiazol-5-yl) group;

Particularly preferred compounds include those in which, independently or in any compatible combination;

W represents pyrid-3-yl, 2-methylbenzimidazol-1-yl, 2-methylimidazo[4,5-c]pyridin-1-yl, 2-methylimidazo[4,5-c]pyridin-3-yl and 2-methylimidazo[4,5-c]pyridin-5-yl;

Z represents an alkanediyl ((for example propylene, 2-hydroxypropylene, 1-methylpropylene, 1,1-dimethylpropylene, butylene, 1-methylbutylene, 1,1-dimethylbutylene, 3-hydroxybutylene, pentylene, 1-methylpentylene, 1,1-dimethylpentylene, 4-methoxypentylene, hexylene, 1,1-dimethylhexylene, heptylene, 1-methylheptylene, 1,1-dimethylheptylene, octylene, 1,1-dimethyloctylene, nonylene, decylene, undecylene)) group or a $-(CH_2)_qU(CH_2)_r-$ (for example a

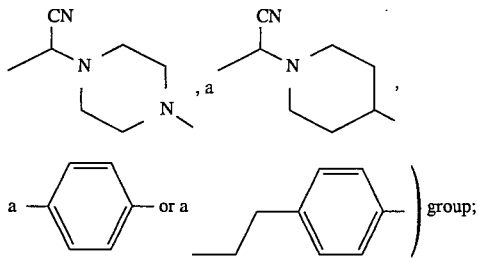

group;

$R^1$ represents a hydrogen atom, a $-C_1-C_6$ alkyl (for example methyl, ethyl) group, a $-C_2-C_6$ alkenyl (for example allyl) group, or a $-CO_2C_1-C_6$ alkyl (for example ethoxycarbonyl) group;

Q represents a carbonyl or sulphonyl group;

$R^3$ represents the side chain of the amino acid leucine;

Exemplary compounds include:
1. (A) N-6-(2-Methylimidazo[4,5-c]pyridin-3-yl)hexanoyl-L-leucine ethyl ester,
   (B) N-6-(2-Methylimidazo[4,5-c]pyridin-1-yl)hexanoyl-L-leucine ethyl ester,
2. N-6-(2-Methylimidazo[4,5-c]pyridin-1-yl)hexanoyl-D-leucine ethyl ester,
3. N-6-(2-Methylimidazo[4,5-c]pyridin-1-yl)hexanoyl-L-phenylalanine ethyl ester,
4. N-6-(2-Methylimidazo[4,5-c]pyridin-1-yl)hexanoyl-L-leucine propyl ester,
5. N-6-(2-Methylimidazo[4,5-c]pyridin-1-yl)hexanoyl-L-norleucine ethyl ester,
6. N-6-(2-Methylimidazo[4,5-c]pyridin-1-yl)hexanoyl-O-benzyl-L-serine methyl ester,
7. N-6-(2-Methylimidazo[4,5-c]pyridin-1-yl)-2-methylhexanoyl-L-leucine ethyl ester,
8. N-6-(2-Methylimidazo[4,5-c]pyridin-1-yl)-2,2-dimethylhexanoyl-L-leucine ethyl ester,
9. N-6-(2-Methylimidazo[4,5-c]pyridin-1-yl)-5-hydroxyhexanoyl-L-leucine ethyl ester,
10. N-6-(2-Methylimidazo[4,5-c]pyridin-1-yl)hexanoyl-L-leucine hexadecyl ester,
11. (A) N-4-(2-Methylimidazo[4,5-c]pyridin-3-yl)butanoyl-L-leucine ethyl ester,
    (B) N-4-(2-Methylimidazo[4,5-c]pyridin-1-yl)butanoyl-L-leucine ethyl ester,
    (C) N-4-(2-Methylimidazo[4,5-c]pyridin-5-yl)butanoyl-L-leucine ethyl ester,
12. N-4-(2-Methylimidazo[4,5-c]pyridin-1-yl)butanoyl-L-leucine methyl ester,
13. N-4-(2-Methylimidazo[4,5-c]pyridin-1-yl)butanoyl-O-methyl-L-tyrosine ethyl ester,
14. N-4-(2-Methylimidazo[4,5-c]pyridin-1-yl)butanoyl-L-methionine ethyl ester,
15. N-4-(2-Methylimidazo[4,5-c]pyridin-1-yl)butanoyl-L-norleucine n-butyl ester,
16. N-4-(2-Methylimidazo[4,5-c]pyridin-1-yl)-2,2-dimethylbutanoyl-L-leucine ethyl ester,
17. N-4-(2-Methylimidazo[4,5-c]pyridin-1-yl)-3-hydroxybutanoyl-L-leucine ethyl ester,
18. N-4-(2-Methylimidazo[4,5-c]pyridin-1-yl)butanoyl-L-valine ethyl ester,
19. N-4-(2-Methylimidazo[4,5-c]pyridin-1-yl)butanoyl-L-leucine hexyl ester,
20. N-4-(2-Methylimidazo[4,5-c]pyridin-1-yl)butanoyl-L-leucine decyl ester,
21. N-3-(2-Methylbenzimidazol-1-yl)propylsulphonyl-L-leucine ethyl ester,
22. N-4-(2-Methylimidazo[4,5-c]pyridin-1-yl)propylsulphonyl-L-alanine ethyl ester,
23. N-4-(2-Methylimidazo[4,5-c]pyridin-1-yl)propylsulphonyl-L-isoleucine ethyl ester,
24. N-4-(2-Methylimidazo[4,5-c]pyridin-1-yl)propylsulphonyl-L-norleucine ethyl ester,
25. N-4-(2-Methylimidazo[4,5-c]pyridin-1-yl)propylsulphonyl-L-methionine ethyl ester,
26. N-4-(2-Methylimidazo[4,5-c]pyridin-1-yl)propylsulphonyl-L-leucine i-propyl ester,
27. N-4-(2-Methylimidazo[4,5-c]pyridin-1-yl)propylsulphonyl-L-leucine pentyl ester,
28. N-4-(2-Methylimidazo[4,5-c]pyridin-1-yl)propylsulphonyl-L-leucine octyl ester,
29. N-4-(2-Methylimidazo[4,5-c]pyridin-1-yl)propylsulphonyl-L-leucine dodecyl ester,
30. N-4-(2-Methylimidazo[4,5-c]pyridin-1-yl)propylsulphonyl-L-leucine pentadecyl ester,
31. N-4-(2-Methylimidazo[4,5-c]pyridin-1-yl)propylsulphonyl-L-leucine hexadecyl ester,
32. N-4-(2-Methylimidazo[4,5-c]pyridin-1-yl)propylsulphonyl-L-leucine octadecyl ester,
33. (A) N-4-(2-Methylimidazo[4,5-c]pyridin-3-yl)propylsulphonyl-L-leucinyl ethyl ether,
    (B) N-4-(2-Methylimidazo[4,5-c]pyridin-1-yl)propylsulphonyl-L-leucinyl ethyl ether,
    (C) N-4-(2-Methylimidazo[4,5-c]pyridin-5-yl)propylsulphonyl-L-leucinyl ethyl ether,
34. N-4-(2-Methylimidazo[4,5-c]pyridin-1-yl)propylsulphonyl-L-leucinyl methyl ether,
35. N-4-(2-Methylimidazo[4,5-c]pyridin-1-yl)propylsulphonyl-L-leucinyl octyl ether,
36. N-4-(2-Methylimidazo[4,5-c]pyridin-1-yl)propylsulphonyl-L-leucinyl hexadecyl ether,
37. N-4-(2-Methylimidazo[4,5-c]pyridin-1-yl)propylsulphonyl-L-leucinyl benzyl ether,
38. N-4-(2-Methylimidazo[4,5-c]pyridin-1-yl)propylsulphonyl-L-leucinyl propionate,
39. N-4-(2-Methylimidazo[4,5-c]pyridin-1-yl)propylsulphonyl-L-leucinyl octadecanoate,
40. N-4-(2-Methylimidazo[4,5-c]pyridin-1-yl)propylsulphonyl-L-leucinyl N'-ethyl carbamate,
41. N-4-(2-Methylimidazo[4,5-c]pyridin-1-yl)propylsulphonyl-L-leucinyl N'-benzyl carbamate,
42. N-4-(2-Methylimidazo[4,5-c]pyridin-1-yl)propylsulphonyl-L-leucinyl N'-2-pyridylcarbamate,
43. N-4-(2-Methylimidazo[4,5-c]pyridin-1-yl)propylsulphonyl-L-leucinyl N-octadecylcarbamate,
44. N-4-(2-Methylimidazo[4,5-c]pyridin-1-yl)propylsulphonyl-1-(3-ethyl- 1,2,4-oxadiazol-5-yl)-3-methylbutylamine,
45. (A) N-5-(2-Methylimidazo[4,5-c]pyridin-3-yl)pentanoyl-L-leucine ethyl ester,
    (B) N-5-(2-Methylimidazo[4,5-c]pyridin-1-yl)pentanoyl-L-leucine ethyl ester, 46. N-5-(2-Methylimidazo[4,5-c]pyridin-1-yl)pentanoyl-L-leucine i-propyl ester,
47. N-5-(2-Methylimidazo[4,5-c]pyridin-1-yl)pentanoyl-O-methyl-L-tyrosine ethyl ester,
48. N-5-(2-Methylimidazo[4,5-c]pyridin-1-yl)pentanoyl-D, L-allylglycine ethyl ester,
49. N-5-(2-Methylimidazo[4,5-c]pyridin-1-yl)pentanoyl-L-norleucine allyl ester,
50. N-5-(2-Methylimidazo[4,5-c]pyridin-1-yl)-2-methylpentanoyl-L-leucinyl ethyl ether,
51. N-5-(2-Methylimidazo[4,5-c]pyridin-1-yl)-2,2-dimethylpentanoyl-L-leucine 2-benzoxyethylethyl ester,
52. N-5-(2-Methylimidazo[4,5-c]pyridin-1-yl)-3-hydroxypentanoyl-L-leucine 2-(2-ethoxyethoxy)ethyl ester,
53. N-5-(2-Methylimidazo[4,5-c]pyridin-1-yl)pentanoyl-1-(3-methyl-1,2,4-oxadiazol-5-yl)-3-methylbutylamine,
54. N-5-(2-Methylimidazo[4,5-c]pyridin-1-yl)pentanoyl-1-(6-ethylpyrazin-2-yl)-3-methylbutylamine,
55. N-5-(2-Methylimidazo[4,5-c]pyridin-1-yl)pentanoyl-L-leucinyl N'-ethylcarbamate,
56. (A) N-Methyl-N-6-(2-methylimidazo[4,5-c]pyridin-3-yl)hexanoyl-L-leucine ethyl ester,
  (B) N-Methyl-N-6-(2-methylimidazo[4,5-c]pyridin-1-yl)-hexanoyl-L-leucine ethyl ester,
  (C) N-Methyl-N-6-(2-methylimidazo[4,5-c]pyridin-5-yl)-hexanoyl-L-leucine ethyl ester,
57. (A) N-Methyl-N-6-(2-methylimidazo[4,5-c]pyridin-3-yl)hexanoyl-L-isoleucine allyl ester,
  (B) N-Methyl-N-6-(2-methylimidazo[4,5-c]pyridin-1-yl)-hexanoyl-L-isoleucine allyl ester,
  (C) N-Methyl-N-6-(2-methylimidazo[4,5-c]pyridin-5-yl)-hexanoyl-L-isoleucine allyl ester,
58. (A) N-Methyl-N-6-(2-methylimidazo[4,5-c]pyridin-3-yl)hexanoyl-L-leucinyl ethyl ether,
  (B) N-Methyl-N-6-(2-methylimidazo[4,5-c]pyridin-1-yl)-hexanoyl-L-leucinyl ethyl ether,
  (C) N-Methyl-N-6-(2-methylimidazo[4,5-c]pyridin-5-yl)hexanoyl-L-leucinyl ethyl ether,
59. N-Methyl-N-6-(2-methylimidazo[4,5-c]pyridin-1-yl)-hexanoyl-L-leucinyl hexadecyl ether,
60. N-Methyl-N-6-(2-methylimidazo[4,5-c]pyridin-1-yl)-hexanoyl-L-phenylalaninyl ethyl ether,
61. N-Methyl-N-6-(2-methylimidazo[4,5-c]pyridin-1-yl)-hexanoyl-L-leucinyl 4-methoxybenzyl ether,
62. N-Methyl-N-6-(2-methylimidazo[4,5-c]pyridin-1-yl)-hexanoyl-L-norleucinyl ethyl ether,
63. N-Methyl-N-6-(2-methylimidazo[4,5-c]pyridin-1-yl)-hexanoyl-O-benzyl-L-serinyl ethyl ether,
64. N-Methyl-N-6-(2-methylimidazo[4,5-c]pyridin-1-yl)-2-methylhexanoyl-L-leucinyl ethyl ether,
65. N-Ethoxycarbonyl-N-6-(2-methylimidazo[4,5-c]pyridin-1-yl)hexanoyl-L-leucinyl ethyl ether,
66. N-Methyl-N-6-(2-methylimidazo[4,5-c]pyridin-1-yl)-5-methoxyhexanoyl-L-leucinyl ethyl ether,
67. N-Methyl-N-6-(2-methylimidazo[4,5-c]pyridin-1-yl)-hexanoyl-1-(3-ethyl-1,2,4-oxadiazol-5-yl)-3-methylbutylamine,
68. N-Methyl-N-4-(2-methylimidazo[4,5-c]pyridin-1-yl)butanoyl-L-leucine ethyl ester,
69. N-Allyl-N-4-(2-methylimidazo[4,5-c]pyridin-1-yl)butanoyl-L-leucine i-propyl ester,
70. N-Methyl-N-4-(2-methylimidazo[4,5-c]pyridin-1-yl)butanoyl-L-leucinyl ethyl ether,
71. N-Methyl-N-4-(2-methylimidazo[4,5-c]pyridin-1-yl)-2-methylbutanoyl-L-leucinyl ethyl ether,
72. N-Methyl-N-5-(2-methylimidazo[4,5-c]pyridin-1-yl)-pentanoyl-L-leucine ethyl ester,
73. N-Methyl-N-5-(2-methylimidazo[4,5-c]pyridin-1-yl)-pentanoyl-L-leucinyl ethyl ether,
74. N-Methyl-N-5-(2-methylimidazo[4,5-c]pyridin-1-yl)-2-methylpentanoyl-L-leucinyl ethyl ether,
75. N-Methyl-N-5-(2-methylimidazo[4,5-c]pyridin-1-yl)-pentanoyl-L-leucinyl hexadecyl ether,
76. N-Methyl-N-3-(2-methylimidazo[4,5-c]pyridin-1-yl)-propylsulphonyl-L-leucine ethyl ester,
77. N-Methyl-N-3-(2-methylimidazo[4,5-c]pyridin-1-yl)-propylsulphonyl-L-leucine i-propyl ester,
78. N-Methyl-N-3-(2-methylimidazo[4,5-c]pyridin-1-yl)-propylsulphonyl-L-leucinyl ethyl ether,
79. N-Methyl-N-3-(2-methylimidazo[4,5-c]pyridin-1-yl)-propylsulphonyl-L-leucinyl hexadecyl ester,
80. N-Methyl-N-3-(2-methylimidazo[4,5-c]pyridin-1-yl)propylsulphonyl-1-(3-ethyl-1,2,4-oxadiazol-5-yl)-3-methylbutylamine,
81. N-Methyl-N-4-(2-methylimidazo[4,5-c]pyridin-1-yl)butylsulphonyl-L-leucine ethyl ester,
82. N-Methyl-N-4-(2-methylimidazo[4,5-c]pyridin-1-yl)butylsulphonyl-L-leucinyl ethyl ether,
83. N-Methyl-N-4-(2-methylimidazo[4,5-c]pyridin-1-yl)butylsulphonyl-L-leucinyl heptadecyl ether,
84. N-Methyl-N-5-(2-methylimidazo[4,5-c]pyridin-1-yl)-pentylsulphonyl-L-leucine ethyl ester,
85. N-Methyl-N-5-(2-methylimidazo[4,5-c]pyridin-1-yl)-pentylsulphonyl-L-leucine i-propyl ester,
86. N-Methyl-N-5-(2-methylimidazo[4,5-c]pyridin-1-yl)-pentylsulphonyl-L-leucinyl ethyl ether,
87. (A) N-8-(2-Methylimidazo[4,5-c]pyridin-3-yl)octanoyl-L-leucine ethyl ester,
  (B) N-8-(2-Methylimidazo[4,5-c]pyridin-1-yl)octanoyl-L-leucine ethyl ester,
  (C) N-8-(2-Methylimidazo[4,5-c]pyridin-5-yl)octanoyl-L-leucine ethyl ester,
88. N-8-(2-Methylimidazo[4,5-c]pyridin-1-yl)-2-methyloctanoyl-L-leucine ethyl ester,
89. N-8-(2-Methylimidazo[4,5-c]pyridin-1-yl)-2,2-dimethyloctanoyl-L-phenylalanine ethyl ester,
90. N-Methyl-N-8-(2-methylimidazo[4,5-c]pyridin-1-yl)octanoyl-L-leucine i-propyl ester,
91. N-Methyl-N-8-(2-methylimidazo[4,5-c]pyridin-1-yl)octanoyl-L-leucinyl ethyl ether,
92. N-Methyl-N-8-(2-methylimidazo[4,5-c]pyridin-1-yl)octanoyl-1-(3-ethyl-1,2,4-oxadiazol-5-yl)-3-methylbutylamine,
93. N-7-(2-Methylimidazo[4,5-c]pyridin-1-yl)heptanoyl-L-leucine ethyl ester,
94. N-Methyl-N-7-(2-methylimidazo[4,5-c]pyridin-1-yl)-heptanoyl-L-leucinyl ethyl ether,
95. N-Methyl-N-7-(2-methylimidazo[4,5-c]pyridin-1-yl)-2,2-dimethyl-heptanoyl-L-leucinyl ethyl ether,
96. N-Methyl-N-7-(2-methylimidazo[4,5-c]pyridin-1-yl)-heptanoyl-L-leucinyl N'-hexadecylcarbamate,
97. N-11-(2-Methylbenzimidazol-1-yl)undecanoyl-L-leucine ethyl ester,
98. (A) N-11-(2-Methylimidazo[4,5-c]pyridin-3-yl)undecanoyl-L-leucine ethyl ester,
  (B) N-11-(2-Methylimidazo[4,5-c]pyridin-1-yl)undecanoyl-L-leucine ethyl ester,
99. N-9-(2-Methylimidazo[4,5-c]pyridin-1-yl)nonanoyl-L-leucine ethyl ester,
100. N-Methyl-N-9-(2-methylimidazo[4,5-c]pyridin-1-yl)-nonanoyl-L-leucine i-propyl ester,
101. N-Methyl-N-9-(2-methylimidazo[4,5-c]pyridin-1-yl)-nonanoyl-L-leucinyl ethyl ether,
102. N-Methyl-N-9-(2-methylimidazo[4,5-c]pyridin-1-yl)-2,2-dimethylnonanoyl-L-leucinyl ethyl ether, 103. N-Methyl-N-10-(2-methylimidazo[4,5-c]pyridin-1-yl)-decanoyl-L-leucinyl ethyl ester,
104. N-Methyl-N-10-(2-methylimidazo[4,5-c]pyridin-1-yl)-decanoyl-L-leucine ethyl ester,
105. N-Methyl-N-11-(2-methylimidazo[4,5-c]pyridin-1-yl)undecanoyl-L-leucine ethyl ester,
106. N-Methyl-N-11-(2-methylimidazo[4,5-c]pyridin-1-yl)undecanoyl-L-leucinyl ethyl ether,
107. N-Methyl-N-12-(2-methylimidazo[4,5-c]pyridin-1-yl)-dodecanoyl-L-leucinyl ethyl ether,
108. N-Methyl-N-6-(2-methylimidazo[4,5-c]pyridin-1-yl)-hexanoyl-D-leucine ethyl ester,
109. N-Methyl-N-6-(2-methylimidazo[4,5-c]pyridin-1-yl)-hexanoyl-L-phenylalanine ethyl ester,
110. N-Methyl-N-6-(2-methylimidazo[4,5-c]pyridin-1-yl)-hexanoyl-L-leucine,
111. N-Methyl-N-6-(2-methylimidazo[4,5-c]pyridin-5-yl)-hexanoyl-L-leucine,
112. N-Methyl-N-6-(2-methylimidazo[4,5-c]pyridin-3-yl)-hexanoyl-L-isoleucine,
113. N-6-(2-Methylimidazo[4,5-c]pyridin-1-yl)hexanoyl-L-leucine,
114. N-6-(2- Methylimidazo[4,5-c]pyridin-1-yl)hexanoyl-L-phenylalanine,
115. N-4-(2-Methylimidazo[4,5-c]pyridin-1-yl)butanoyl-L-leucine,
116. N-4-(2-Methylimidazo[4,5-c]pyridin-1-yl)propylsulphonyl-L-methionine,
117. N-8-(2-Methylimidazo[4,5-c]pyridin-1-yl)octanoyl-L-leucine,
118. N-Methyl-N-8-(2-methylimidazo[4,5-c]pyridin-1-yl)octanoyl-L-leucine,
119. N-Methyl-N-11-(2-methylimidazo[4,5-c]pyridin-1-yl)undecanoyl-L-leucine,
120. N-Methyl-N-4-(2-methylimidazo[4,5-c]pyridin-1-yl)-benzoyl-L-leucine ethyl ester,
121. N-Methyl-N-4-(2-methylimidazo[4,5-c]pyridin-1-yl)-benzoyl-L-leucinyl ethyl ether,
122. N-Methyl-N-4-(2-methylimidazo[4,5-c]pyridin-1-yl)-benzoyl-L-phenylalanine ethyl ester,
123. N-Methyl-N-4-(2-methylimidazo[4,5-c]pyridin-1-yl)-benzoyl-L-leucine n-butyl ester,
124. N-Methyl-N-4-(2-methylimidazo[4,5-c]pyridin-1-yl)-benzoyl-L-isoleucine ethyl ester,
125. N-Ethyl-N-4-(2-methylimidazo[4,5-c]pyridin-1-yl)-benzoyl-L-leucine ethyl ester,
126. N-Methyl-N-4-(2-methylimidazo[4,5-c]pyridin-1-yl)-benzoyl-L-leucine 2-pyridyl amide,
127. N-Methyl-N-4-(2-methylimidazo[4,5-c]pyridin-1-yl)-benzoyl-L-leucinyl N'-ethylcarbamate,
128. N-Methyl-N-4-(2-methylimidazo[4,5-c]pyridin-1-yl)-benzoyl-L-leucinyl ethanoate,
129. N-Methyl-N-4-(2-methylimidazo[4,5-c]pyridin-1-yl)-benzoyl-1-(3-ethyl- 1,2,4-oxadiazol-5-yl)-3-methylbutylamine,
130. N-Methyl-N-4-(2-(3-pyridyl)ethyl)benzoyl-L-leucine ethyl ester,
131. N-Methyl-N-4-(2-(3-pyridyl)ethyl)benzoyl-L-leucinyl ethyl ether,
132. N-Methyl-N-4-(2-(3-pyridyl)ethyl)benzoyl-L-leucine i-propyl ester,
133. N-Ethyl-N-4-(2-(3-pyridyl)ethyl)benzoyl-L-leucine ethyl ester,
134. N-Methyl-N-4-(2-(3-pyridyl)ethyl)benzoyl-L-norleucinyl ethyl ether,
135. N-Methyl-N-4-(2-(3-pyridyl)ethyl)benzoyl-1-tetrahydrofuryl-3-methylbutylamine,
136. N-Methyl-N-4-(2-(3-pyridyl)ethyl)benzoyl-L-valine ethyl ester,
137. N-Methyl-N-4-(2-(3-pyridyl)ethyl)benzoyl-N'-methyl-L-tryptophan ethyl ester,
138. N-Methyl-N-4-(2-(3-pyridyl)ethyl)benzoyl-O-benzyl-L-serine ethyl ester,
139. N-Methyl-N-4-(2-(3-pyridyl)ethyl)benzoyl-L-isoleucinyl ethyl ether,
140. N-4-(3-Pyridylcyanomethyl)piperazinecarbonyl-L-leucine ethyl ester,
141. N-4-(3-Pyridylcyanomethyl)piperazinecarbonyl-L-leucine ethyl ester,
142. N-Methyl-N-4-(3-pyridylcyanomethyl)piperazinecarbonyl-L-leucine ethyl ester,
143. N-Methyl-N-4-(3-pyridylcyanomethyl)piperazinecarbonyl-L-leucinyl ethyl ether,
144. N-Methyl-N-4-(3-pyridylcyanomethyl)piperidinecarbonyl-L-leucine ethyl ester,
145. N-Methyl-N-4-(3-pyridylcyanomethyl)piperidinecarbonyl-L-leucinyl ethyl ether,
146. N-Methyl-N-4-(3-pyridylcyanomethyl)piperidinecarbonyl-L-leucine propyl ester,
147. N-Methyl-N-4-(3-pyridylcyanomethyl)piperidinecarbonyl-L-isoleucine ethyl ester,
148. N-Methyl-N-4-(3-pyridylcyanomethyl)piperidinecarbonyl-L-phenylalanine ethyl ester,
149. N-Ethyl-N-4-(3-pyridylcyanomethyl)piperidinecarbonyl-L-leucinyl ethyl ether;
or a salt of such a compound.

Compounds of general formula I may be prepared by any suitable method known in the art and/or by the following process, which itself forms part of the invention.

According to a second aspect of the invention, there is provided a process for preparing a compound of general formula I as defined above, the process comprising:

(a) treating a nitrogen heterocycle represented by general formula II

W—H          II wherein W is as defined in general formula I, with a suitable base (e.g. sodium hydride, potassium hydride or sodium bis(trimethylsilyl)amide), followed by a compound of general formula III

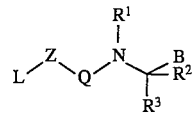

III wherein Z, Q, $R^1$, $R^2$, $R^3$ and B are as defined in general formula I, and L is a leaving group such as chloro, bromo, iodo, methanesulphonyloxy, p-toluenesulphonyloxy or trifluoromethanesulphonyloxy;

(b) treating an amine represented by general formula IV

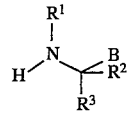

IV wherein $R^1$, $R^2$, $R^3$, and B are as defined in general formula I, with a suitable base in an aprotic solvent followed by a halo derivative of general formula V

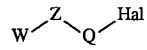

V wherein W, Z and Q are as defined in general formula I and Hal is a halide such as fluoro, chloro, bromo or iodo;

(c) treating an amine of general formula IV with a derivative of general formula VI

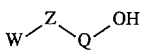   VI wherein W and Z are as defined in general formula I and Q represents a —C(=O)— group, in the presence of a coupling reagent; and (d) optionally after step (a), step (b) or step (c) convening, in one or a plurality of steps, a compound of general formula I into another compound of general formula I.

The reaction of step (a) can, for preference, be conducted in an aprotic solvent, for example tetrahydrofuran, to yield compounds of general formula I. The reaction may yield an isomeric mixture, which may be separated by chromatography to yield compounds of general formula I.

The reaction of step (b) can, for preference, be conducted in an aprotic solvent, for example tetrahydrofuran, to yield compounds of general formula I. Suitable bases include sodium hydride, potassium hydride or sodium bis(trimethylsilyl)amide when Q is a bond and triethylamine when Q is a carbonyl, thiocarbonyl or sulphonyl group.

The coupling reagent used in the reaction of step (c) can, for preference, be N,N'-dicyclohexylcarbodiimide to yield compounds of general formula I.

By means of step (d), compounds of general formula I wherein B is a —$CO_2R^8$ group can be converted to compounds of general formula I in which B is a —$CO_2H$ group by acid or base catalysed hydrolysis in a protic solvent. Suitable acids for use in the hydrolysis include sulphuric and hydrochloric acids, whilst base hydrolysis can be catalysed with sodium or potassium hydroxide. If B represents a —$CO_2R^8$ group in which $R^8$ is a benzyl group, the conversion of B from an ester to an acid can also be effected by hydrogenation in a suitable solvent, for example, a lower alcohol such as ethanol using a noble metal catalyst such as palladium or platinum.

Also by means of step (d) compounds of general formula I wherein B is a —$CONR^9R^{10}$ group wherein $R^9$ and $R^{10}$ are as defined in general formula I, may be prepared by the following methods;

i) by treatment of a compound of general formula I wherein B is a —$CO_2H$ group with an amine of general formula $HNR^9R^{10}$ in the presence of a coupling reagent (e.g. N,N'-dicyclohexylcarbodiimide);

ii) by treatment of a compound of general formula I wherein B is a —$CO_2R^8$ group wherein $R^8$ is a —$C_1$-$C_6$ alkyl with a dimethylaluminium amide of general formula VII $(Me)_2AlNR^9R^{10}$   VII wherein $R^9$ and $R^{10}$ are as defined in general formula I, which is prepared in situ from trimethylaluminium and an amine of general formula $HNR^9R^{10}$.

Also by means of step (d) compounds of general formula I may be prepared by the treatment of a compound of general formula I wherein $R^1$ is hydrogen with base followed by an electrophile of general formula VIII $LR^1$   VIII wherein $R^1$ is as defined in general formula I but is not a hydrogen atom, a phenyl or a substituted phenyl group, and L is as defined in general formula III. Electrophiles of general formula VIII are available in the art or can be prepared by procedures known to those skilled in the art.

Also by means of step (d) certain compounds of general formula I wherein B is a $VR^8$ group wherein V is —$CH_2O$— and $R^8$ is hydrogen may be prepared by treatment of a compound of general formula I wherein B is a $VR^8$ group wherein V is —C(=O)O— and $R^8$ is other than hydrogen with a suitable reducing agent (e.g. lithium aluminium hydride).

Also by means of step (d) certain compounds of general formula I wherein B is a $VR^8$ group wherein V is —$CH_2O$— and $R^8$ is other than hydrogen may be prepared by treatment of a compound of general formula I wherein B is a $VR^8$ group wherein V is —$CH_2O$— and $R^8$ is hydrogen with a suitable base in an aprotic solvent followed by an electrophile of general formula $LR^8$ wherein $R^8$ is —$C_1$-$C_{18}$ alkyl optionally substituted by one or more halogen atoms, —$C_3$-$C_{18}$ alkenyl, —$C_3$-$C_{18}$ alkynyl, —($C_1$-$C_6$ alkyl)O$C_1$-$C_6$ alkyl, —($C_1$-$C_6$ alkyl)S$C_1$-$C_6$ alkyl, —($C_1$-$C_6$ alkyl)O($C_1$-$C_6$ alkyl)O$C_1$-$C_6$ alkyl, —$C_3$-$C_8$ cycloalkyl, —$C_4$-$C_8$ cycloalkenyl, a group —D (wherein or n is an integer of 1, 2 or 3) or a —($C_1$-$C_6$ alkyl)OD group and L is a leaving group as defined above.

Also by means of a step (d) certain compounds of general formula I wherein B is a $VR^8$ group wherein V is a —$CH_2O$(C=O)— group and $R^8$ is as defined in general formula I but is not hydrogen, may be prepared by treatment of a compound of general formula I wherein B is a $VR^8$ group wherein V is a —$CH_2O$— group and $R^8$ is hydrogen with a compound of general formula LC(=O)$R^8$ wherein L is as defined above and $R^8$ is as defined in general formula I but is not hydrogen, in an aprotic solvent (e.g. tetrahydrofuran) in the presence of a suitable base (e.g. triethylamine).

Also by means of a step (d) certain compounds of general formula I wherein B is a $VR^8$ group wherein V is a —$CH_2O$(C=O)NH— group and $R^8$ is as defined in general formula I but is not hydrogen, may be prepared by treatment of a compound of general formula I wherein B is a $VR^8$ group wherein V is a —$CH_2O$— group and $R^8$ is hydrogen with a compound of general formula OCN$R^8$ wherein $R^8$ is as defined in general formula I but is not hydrogen.

Also by means of a step (d) certain compounds of general formula I wherein B is a 1,2,4-oxadiazol-5-yl group may be prepared by treatment of a compound of general formula I wherein B is a —$CO_2R^8$ group wherein $R^8$ is hydrogen with pentafluorophenol and a coupling agent such as N-(3-dimethylaminopropyl)-N'-ethylcarodiimide in a solvent such as dichloromethane. The resulting pentafluorophenyl ester is treated with an amide oxime of general formula IX

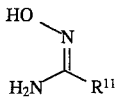   IX wherein $R^{11}$ represents hydrogen, —$C_1$-$C_6$ alkyl, halogen, —$CF_3$ or —CN, in a suitable aprotic solvent (e.g. chloroform), followed by cyclisation under Dean-Stark conditions in suitable solvent (e.g. xylene, toluene, benzene or ethyl acetate). The cyclisation may be aided by the addition of activated molecular sieves. Amide oximes of general formula IX are known in the art or may be prepared by methods analogous to those known in the art.

Compounds of general formula II are known in the art or may be prepared by methods analogous to those known in the art.

Compounds of general formula III may be prepared by treatment of an amine of general formula IV with an activated carboxylic, thiocarboxylic or sulphonic acid of general formula X

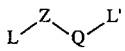

wherein Z, and Q are as defined in general formula I, L is as defined above and L' is as defined above for L, in the presence of a suitable base (e.g. triethylamine). Amines of general formula IV and activated carboxylic, thiocarboxylic or sulphonic acids of general formula X are known in the art or may be prepared by methods known in the art.

Compounds of general formula V wherein W, Z and Q are as defined in general formula I, and Hal is chloro may be prepared by the treatment of a compound of general formula VI with thionyl chloride (or oxalyl chloride). The reaction may be aided by the addition of catalytic N,N-dimethylformamide.

Compounds of general formula VI may be prepared by the treatment of a compound of general formula II with a suitable base (e.g. sodium hydride, potassium hydride or sodium bis(trimethylsilyl)amide), followed by a compound of general formula XI

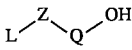

wherein Z and Q are as defined in general formula I and L is a leaving group as defined above. Compounds of general formula XI are known in the art or may be prepared by methods known in the art.

The appropriate solvents employed in the above reactions are solvents wherein the reactants are soluble but which do not react with the reactants. The preferred solvents vary from reaction to reaction and are readily ascertained by one of ordinary skill in the art.

Compounds of general formula III, general formula V and general formula VI are valuable intermediates in the preparation of compounds of general formula I, as are other novel compounds specifically or generically disclosed herein. According to a third aspect of the invention, there is therefore provided a compound of general formula III. According to a fourth aspect of the invention, there is therefore provided a compound of general formula V. According to a fifth aspect of the invention, there is therefore provided a compound of general formula VI.

Compounds of general formula I are potentially useful as PAF antagonists.

This invention therefore also relates to methods of treatment for patients (or animals including mammalian animals raised in the dairy, meat, or fur trades, or as pets) suffering from disorders or diseases which can be attributed to PAF as previously described. More specifically, the invention relates to a method of treatment involving the administration of PAF antagonists of general formula I as the active ingredient. In addition to the treatment of warm blooded animals such as mice, rats, horses, cattle, pigs, sheep, dogs, cats, etc., the compounds of the invention are effective in the treatment of humans.

According to a sixth aspect of the invention there is provided a compound of general formula I for use in human or veterinary medicine particularly in the management of diseases mediated by PAF. When used as PAF antagonists, the compounds of general formula I can be used among other things to reduce inflammation and pain, to correct respiratory, cardiovascular, and intravascular alterations or disorders, and to regulate the activation or coagulation of platelets, to correct hypotension during shock, the pathogenesis of immune complex deposition and smooth muscle contractions.

According to a seventh aspect of the invention there is provided the use of a compound of general formula I in the preparation of an agent for the treatment or prophylaxis of PAF-mediated diseases, and/or the treatment of inflammatory disorders such as rheumatoid arthritis, osteoarthritis and eye inflammation, cardiovascular disorder, thrombocytopenia, asthma, endotoxin shock, adult respiratory distress syndrome, glomerulonephritis, immune regulation, gastric ulceration, transplant rejection, psoriasis, allergic dermatitis, urticaria, multiple sclerosis, cerebral, myocardial and renal ischemia and any other condition in which PAF is implicated.

Compounds of general formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

According to a eighth aspect of the invention there is provided a pharmaceutical or veterinary formulation comprising a compound of general formula I and a pharmaceutically and/or veterinarily acceptable carrier. One or more compounds of general formula I may be present in association with one or more non-toxic pharmaceutically and/or veterinarily acceptable carriers and/or diluents and/or adjuvants and if desired other active ingredients.

The pharmaceutical compositions containing compounds of general formula I may be in a form suitable for oral use, for example, as tablets, troches, lozenges, aqueous or oily suspensions, dispersible powders or granules, emulsions, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occuring phosphatide, for example lecithin, or condensation products of an alkylene oxide with fatty acids for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more colouring agents, one or more flavouring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parentally acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical application to the skin compounds of general formula I may be made up into a cream, ointment, jelly, solution or suspension etc. Cream or ointment formulations that may be used for the drug are conventional formulations well known in the art, for example, as described in standard text books of pharmaceutics such as the British Pharmacopoeia.

For topical applications to the eye, compounds of general formula I may be made up into a solution or suspension in a suitable sterile aqueous or non-aqueous vehicle. Additives, for instance buffers, preservatives including bactericidal and fungicidal agents, such as phenyl mercuric acetate or nitrate, benzalkonium chloride or chlorohexidine, and thickening agents such as hypromellose may also be included.

Compounds of general formula I may be administered parenterally in a sterile medium. The drug depending on the vehicle and concentration used, can either be suspended or dissolved in the vehicle. Advantageously, adjuvants such as a local anaesthetic, preservative and buffering agents can be dissolved in the vehicle.

Compounds of general formula I may be used for the treatment of the respiratory tract by nasal or buccal administration of, for example, aerosols or sprays which can disperse the pharmacological active ingredient in the form of a powder or in the form of drops of a solution or suspension. Pharmaceutical compositions with powder-dispersing properties usually contain, in addition to the active ingredient, a liquid propellant with a boiling point below room temperature and, if desired, adjuncts, such as liquid or solid non-ionic or anionic surfactants and/or diluents. Pharmaceutical compositions in which the pharmacological active ingredient is in solution contain, in addition to this, a suitable propellant, and furthermore, if necessary, an additional solvent and/or a stabiliser. Instead of the propellant, compressed air can also be used, it being possible for this to be produced as required by means of a suitable compression and expansion device.

Dosage levels of the order of from about 0.1 mg to about 140 mg per kilogram of body weight per day are useful in the treatment of the above-indicated conditions (about 0.5 mg to about 7 g per patient per day). For example, inflammation may be effectively treated by the administration of from about 0.01 to 50 mg of the compound per kilogram of body weight per day (about 1.0 mg to about 3.5 g per patient per day). The dosage employed for the topical administration will, of course, depend on the size of the area being treated. For the eyes each dose will be typically in the range from 10 to 100 mg of the drug.

The amount of active ingredient that may be combined with the carder materials to produce a single dosage form will vary depending upon the host treated and the particular mode of administration. For example, a formulation intended for the oral administration of humans may contain from 0.5 mg to 5 g of active agent compounded with an appropriate and convenient amount of carder material which may vary from about 5 to about 95 percent of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

It has been found that the compounds of general formula I exhibit in vitro antagonistic activities with respect to PAF. Compounds of general formula I inhibit PAF-induced functions in both the cellular and tissue levels by changing the PAF binding to its specific receptor site. The ability of compounds of general formula I to inhibit the binding of PAF to its specific receptor binding site on human platelet plasma membranes was measured according to Example 150. The ability of compounds of general formula I to reverse the hypotension caused by an infusion of PAF in rats was measured according Example 151.

The following examples illustrate the invention, but are not intended to limit the scope in any way.

The following abbreviations have been used in the Examples:

DCM—Dichloromethane
DMAP—4-Dimethylaminopyridine
DMF—N,N-dimethylformamide
TDA-1—Tris(2-(2-methoxyethoxy)ethyl)amine
THF—Tetrahydrofuran Unless otherwise stated $^1$H NMR spectra were recorded on a Bruker AC-250 spectrometer at 250 MHz using CDCl$_3$ as a solvent and internal reference and are reported as delta ppm from TMS.

EXAMPLE 1

(A) N-6-(2-Methylimidazo[4,5-c]pyridin-3-yl)hexanoyl-L-leucine ethyl ester and (B) N-6-(2-methylimidazo[4,5-c]pyridin-1-yl)hexanoyl-L-leucine ethyl ester (a) N-6-Bromohexanoyl-L-leucine ethyl ester A stirred suspension of L-leucine ethyl ester hydrochloride (8.38 g, 45 mmol) in dry THF (80 ml) at room temperature was treated with triethylamine (6.3 ml, 45 mmol). The reaction mixture was treated with 6-bromohexanoyl chloride (6.91 ml, 45 mmol). The reaction mixture was stirred for 4 h at room temperature and then diluted with a mixture of saturated aqueous ammonium chloride and ethyl acetate. The organic layer was separated, washed with saturated aqueous ammonium chloride, dried over anhydrous sodium sulphate, filtered and evaporated under reduced pressure to give N-6-bromohexanoyl-L-leucine ethyl ester (12.1 g, 80%) as an oil which was used for the next step without further purification.

delta$_H$ 5.94 (1H, d, J 8.1 Hz), 4.70–4.55 (1H, m), 4.16 (2H, q, J 7.2 Hz), 3.39 (2H, t, J 6.4 Hz), 2.22 (2H, t, J 7.2 Hz), 1.94–1.80 (2H, m), 1.74–1.39 (7H, m), 1.26 (3H, t, J 7.0 Hz), 0.93 (6H, d, J 5.8 Hz).

(b) (A) N-6-(2-Methylimidazo[4,5-c]pyridin-3-yl)hexanoyl-L-leucine ethyl ester and (B) N-6-(2-methylimidazo[4,5-c]pyridin-1-yl)hexanoyl-L-leucine ethyl ester A stirred solution of 2-methylimidazo[4,5-c]pyridine (3.0 g, 22.5 mmol) in dry THF (60 ml) at room temperature was treated with sodium hydride (900 mg, 22.5 ml). The mixture was stirred for 1 h and the resulting white slurry treated with a solution of N-6-bromohexanoyl-L-leucine ethyl ester (22.5 mmol) in dry THF (30 ml) and stirred overnight. The reaction mixture was diluted with a mixture of saturated aqueous ammonium chloride and ethyl acetate. The organic layer was separated, washed with saturated aqueous ammonium chloride, dried over anhydrous sodium sulphate, filtered and evaporated under reduced pressure to give an oil. The crude product mixture was purified by column chromatography (silica: 5% methanol in DCM) and two of the three possible regioisomers were collected, eluting in the order;
(A) N-6-(2-methylimidazo[4,5-c]pyridin-3-yl)hexanoyl-L-leucine ethyl ester

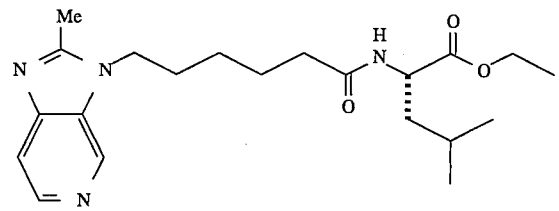

Pale yellow oil (0.7% yield): i.r. (CDCl$_3$) 1725, 1660 cm$^{-1}$ delta$_H$ 8.73 (1H, s), 8.39 (1H, d, J 5.3 Hz), 7.58 (1H, d, J 5.5 Hz), 5.94 (1H, br d, J 8.3 Hz), 4.65–4.54 (1H, m), 4.24–4.11 (4H, m), 2.63 (3H, s), 2.21 (2H, t, J 7.2 Hz), 1.90–1.32 (9H, m), 1.27 (3H, t, J 7.3 Hz), 0.93 (3H, d, J 6.0 Hz), 0.92 (3H, d, J 6.3 Hz);

(B) N-6-(2-methylimidazo[4,5-c]pyridin-1-yl)hexanoyl-L-leucine ethyl ester

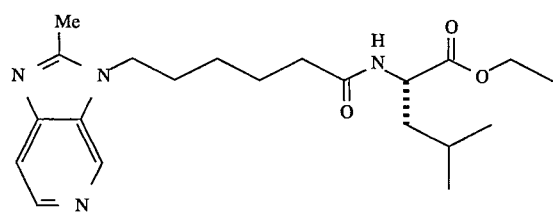

Pale yellow oil (0.7% yield): i.r. (CDCl$_3$) 1725, 1660 cm$^{-1}$ delta$_H$ 8.97 (1H, s), 8.37 (1H, d, J 5.6 Hz), 7.24 (1H, d, 5.5 Hz), 5.92 (1H, br d, J 8.2 Hz), 4.67–4.55 (1H, m), 4.18 (2H, q, J 7.1 Hz), 4.10 (2H, t, J 7.9 Hz), 2.63 (3H, s), 2.22 (2H, t, J 7.2 Hz), 1.90–1.32 (9H, m), 1.28, (3H, t, J 7.2 Hz), 0.94 (3H, d, J 5.9 Hz), 0.93 (3H, d, J 6.2 Hz).

EXAMPLES 2–10

The compounds of Examples 2–10 may be prepared by the method of Example 1 employing the appropriate amino acid derivative in lieu of L-leucine ethyl ester hydrochloride as starting material and for certain compounds the appropriate substituted 6-bromohexanoyl chloride in lieu of 6-bromohexanoyl chloride.

2. N-6-(2-Methylimidazo[4,5-c]pyridin-1-yl)hexanoyl-D-leucine ethyl ester
3. N-6-(2-Methylimidazo[4,5-c]pyridin-1-yl)hexanoyl-L-phenylalanine ethyl ester
4. N-6-(2-Methylimidazo[4,5-c]pyridin-1-yl)hexanoyl-L-leucine propyl ester
5. N-6-(2-Methylimidazo[4,5-c]pyridin-1-yl)hexanoyl-L-norleucine ethyl ester
6. N-6-(2-Methylimidazo[4,5-c]pyridin-1-yl)hexanoyl-O-benzyl-L-serine methyl ester
7. N-6-(2-Methylimidazo[4,5-c]pyridin-1-yl)-2-methylhexanoyl-L-leucine ethyl ester
8. N-6-(2-Methylimidazo[4,5-c]pyridin-1-yl)-2,2-dimethylhexanoyl-L-leucine ethyl ester
9. N-6-(2-Methylimidazo[4,5-c]pyridin-1-yl)-5-hydroxyhexanoyl-L-leucine ethyl ester
10. N-6-(2-Methylimidazo[4,5-c]pyridin-1-yl)hexanoyl-L-leucine hexadecyl ester

EXAMPLE 11

(A) N-4-(2-Methylimidazo[4,5-c]pyridin-3-yl)butanoyl-L-leucine ethyl ester, (B) N-4-(2-methylimidazo[4,5-c]pyridin-1-yl)butanoyl-L-leucine ethyl ester and (C) N-4-(2-methylimidazo[4,5-c]pyridin-5-yl)butanoyl-L-leucine ethyl ester (a) 4-Bromobutanoyl-L-leucine ethyl ester 4-Bromobutanoyl-L-leucine ethyl ester was prepared by the procedure of Example 1 Step (a) employing 4-bromobutanoyl chloride in lieu of 6-bromohexanoyl chloride.

Yellow oil (30% yield): i.r. (CDCl₃) 2210, 1730, 1670, 1500, 1155 cm⁻¹ delta$_H$ 6.34 (1H, d, J 8.2 Hz), 4.63–4.50 (1H, m), 4.14 (2H, q, J 7.1 Hz), 3.44 (2H, t, J 6.0 Hz), 2.40 (2H, t, J 7.0 Hz), 2.22–2.07 (2H, m), 1.69–1.44 (3H, m), 1.23 (3H, t, J 7.1 Hz), 0.90 (6H, d, J 5.9 Hz).

(b) (A) N-4-(2-Methylimidazo[4,5-c]pyridin-3-yl)butanoyl-L-leucine ethyl ester, (B) N-4-(2-methylimidazo[4,5-c]pyridin-1-yl)butanoyl-L-leucine ethyl ester and (C) N-4-(2-methylimidazo[4,5-c]pyridin-5-yl)butanoyl-L-leucine ethyl ester A suspension of potassium hydroxide (2.1 g, 37 mmol) and TDA-1 (4 drops) in dry acetonitrile (250 ml) under argon was stirred at room temperature for 10 min. 2-Methylimidazo[4,5-c]pyridine (5.0 g, 38 mmol) was added, and the reaction mixture heated at 80° C. for 3 h, then cooled to 40° C. A solution of 4-bromobutanoyl-L-leucine ethyl ester (12.0 g, 36 mmol) in dry acetonitrile (250 ml) was added and the reaction mixture stirred at 80° C. overnight and cooled to room temperature. Ethanol (100 ml) was added and the resulting slurry filtered through a short pad of celite. Column chromatography (silica: 2–8% methanol in DCM) gave three regioisomeric products eluting in the order;

(A) N-4-(2-methylimidazo[4,5-c]pyridin-3-yl)butanoyl-L-leucine ethyl ester

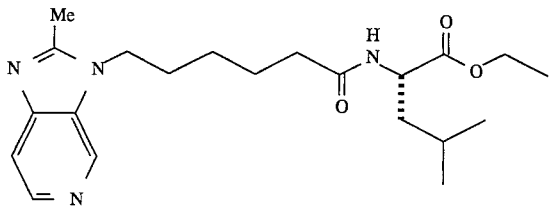

Colourless oil (2% yield): i.r. (CDCl₃) 2210, 1725, 1665, 1500, 1200 cm⁻¹ delta$_H$ 8.69 (1H, s), 8.28 (1H, d, J 5.5 Hz), 7.48 (1H, d, J 5.6 Hz), 7.01 (1H, d, J 8.1 Hz), 4.57–4.48 (1H, m), 4.24–4.18 (2H, m), 4.12 (2H, q, J 7.1 Hz), 2.56 (3H, s), 2.32–2.21 (2H, m), 2.18–2.03 (2H, m), 1.67–1.38 (3H, m), 1.21 (3H, t, J 7.5 Hz), 0.87 (3H, d, J 6.1 Hz), 0.84 (3H, d, J 6.3 Hz); delta$_C$ 173.10, 171.28, 155.13, 147.57, 141.41, 132.82, 132.14, 113.62, 61.17, 50.80, 43.25, 40.97, 31.86, 25.13, 24.78, 22.60, 21.64, 13.99, 13.58;

(B) N-4-(2-methylimidazo[4,5-c]pyridin-1-yl)butanoyl-L-leucine ethyl ester

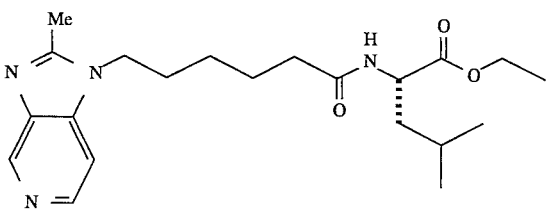

Colourless oil (2% yield): i.r. (CDCl₃) 3445, 2965, 2220, 1730, 1670, 1615, 1510 cm⁻¹ delta$_H$ 8.74 (1H, s), 8.14 (1H, d, J 5.5 Hz), 7.65 (1H, d, J 8.0 Hz), 7.19 (1H, d, J 5.6 Hz), 4.51–4.42 (1H, m), 4.13–3.96 (4H, m), 2.46 (3H, s), 2.23–2.15 (2H, m), 2.07–1.91 (2H, m), 1.61–1.36 (3H, m), 1.34 (3H, t, J 7.1 Hz), 0.80 (3H, d, J 6.1 Hz), 0.75 (3H, d, J 6.2 Hz); delta$_C$ 172.88, 171.32, 153.32, 140.93, 140.68, 139.95, 139.41, 104.92, 59.67, 49.50, 41.64, 39.42, 30.33, 23.61, 23.42, 21.26, 20.20, 12.65, 12.21;

(C) N-4-(2-methylimidazo[4,5-c]pyridin-5-yl)butanoyl-L-leucine ethyl ester

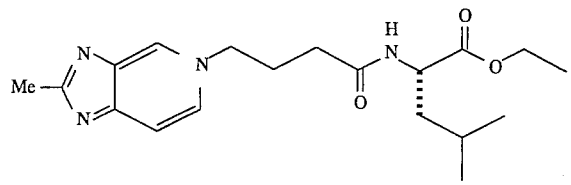

Yellow oil (5% yield): i.r. (CDCl₃) 2190, 1730, 1665, 1315 delta$_H$ 8.41 (1H, s), 8.12 (1H, d, J 7.7 Hz), 7.66 (1H, d, J 8.2 Hz), 7.49 (1H, d, J 6.7 Hz), 4.50–4.25 (3H, m), 4.11 (2H, q, J 7.1 Hz), 2.56 (3H, s), 2.28–2.02 (4H, m) 1.69–1.44 (3H, m), 1.19 (3H, t, J 7.0 Hz), 0.82 (3H, d, J 6.2 Hz), 0.78 (3H, d, J 6.3 Hz) delta$_C$ 173.45, 173.14, 171.44, 155.20, 144.55, 130.30, 128.77, 111.32, 60.94, 58.18, 50.99, 39.97, 30.58, 26.93, 24.67, 22.47, 21.21, 17.67, 13.89.

EXAMPLES 12–20

The compounds of Examples 12–20 may be prepared by the method of Example 11 employing the appropriate amino acid derivative in lieu of L-leucine ethyl ester hydrochloride as starting material and for certain compounds the appropriate substituted 4-bromobutanoyl chloride in lieu of 4-bromobutanoyl chloride.

12. N-4-(2-Methylimidazo[4,5-c]pyridin-1-yl)butanoyl-L-leucine methyl ester
13. N-4-(2-Methylimidazo[4,5-c]pyridin-1-yl)butanoyl-O-methyl-L-tyrosine ethyl ester
14. N-4-(2-Methylimidazo[4,5-c]pyridin-1-yl)butanoyl-L-methionine ethyl ester
15. N-4-(2-Methylimidazo[4,5-c]pyridin-1-yl)butanoyl-L-norleucine n-butyl ester
16. N-4-(2-Methylimidazo[4,5-c]pyridin-1-yl)-2,2-dimethylbutanoyl-L-leucine ethyl ester
17. N-4-(2-Methylimidazo[4,5-c]pyridin-1-yl)-3-hydroxybutanoyl-L-leucine ethyl ester
18. N-4-(2-Methylimidazo[4,5-c]pyridin-1-yl)butanoyl-L-valine ethyl ester
19. N-4-(2-Methylimidazo[4,5-c]pyridin-1-yl)butanoyl-L-leucine hexyl ester
20. N-4-(2-Methylimidazo[4,5-c]pyridin-1-yl)butanoyl-L-leucine decyl ester

EXAMPLE 21

N-3-(2-Methylbenzimidazol-1-yl)propylsulphonyl-L-leucine ethyl ester

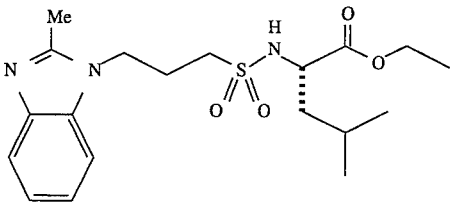

N-3-(2-Methylbenzimidazol-1-yl)propylsulphonyl-L-leucine ethyl ester was prepared by the method of Example 1 employing 3-chloropropylsulphonyl chloride in lieu of 6-bromohexanoyl chloride and 2-methylbenzimidazole in lieu of 2-methylimidazo[4,5-c]pyridine.

Colourles oil (30% yield for last step after chromatography (silica 5% methanol in DCM)): i.r. (CDCl$_3$) 1730 cm$^{-1}$ delta$_H$ (250 MHz, CDCl$_3$) 7.73–7.64 (1H, m), 7.85–7.16 (3H, m), 5.42 (1H, d, J 9.6 Hz), 4.26 (2H, t, J 7.2 Hz), 4.21–3.98 (3H, m), 3.07–2.92 (2H, m), 2.60 (3H, s), 2.40–2.22 (2H, m), 1.90–1.70 (1H, m), 1.68–1.46 (2H, m), 1.23 (3H, t, J 7.1 Hz), 0.92 (3H, d, J 6.5 Hz), 0.90 (3H, d, J 6.6 Hz); delta$_C$ 171.58, 149.87, 140.96, 133.44, 120.96, 120.70, 117.70, 107.57, 60.44, 53.28, 49.08, 40.64, 40.48, 37.10, 23.04, 22.69, 21.35, 19.82, 12.66.

EXAMPLES 22–32

The compounds of Examples 22–32 may be prepared by the method of Example 21 employing the appropriate amino acid derivative in lieu of L-leucine ethyl ester hydrochloride and 2-methylimidazo[4,5-c]pyridine in lieu of 2-methylbenzimidazole as starting materials.

22. N-4-(2-Methylimidazo[4,5-c]pyridin-1-yl)propylsulphonyl-L-alanine ethyl ester
23. N-4-(2-Methylimidazo[4,5-c]pyridin-1-yl)propylsulphonyl-L-isoleucine ethyl ester
24. N-4-(2-Methylimidazo[4,5-c]pyridin-1-yl)propylsulphonyl-L-norleucine ethyl ester
25. N-4-(2-Methylimidazo[4,5-c]pyridin-1-yl)propylsulphonyl-L-methionine ethyl ester
26. N-4-(2-Methylimidazo[4,5-c]pyridin-1-yl)propylsulphonyl-L-leucine i-propyl ester
27. N-4-(2-Methylimidazo[4,5-c]pyridin-1-yl)propylsulphonyl-L-leucine pentyl ester
28. N-4-(2-Methylimidazo[4,5-c]pyridin-1-yl)propylsulphonyl-L-leucine octyl ester
29. N-4-(2-Methylimidazo[4,5-c]pyridin-1-yl)propylsulphonyl-L-leucine dodecyl ester
30. N-4-(2-Methylimidazo[4,5-c]pyridin-1-yl)propylsulphonyl-L-leucine pentadecyl ester
31. N-4-(2-Methylimidazo[4,5-c]pyridin-1-yl)propylsulphonyl-L-leucine hexadecyl ester
32. N-4-(2-Methylimidazo[4,5-c]pyridin-1-yl)propylsulphonyl-L-leucine octadecyl ester

EXAMPLE 33

(A) N-4-(2-Methylimidazo[4,5-c]pyridin-3-yl)propylsulphonyl-L-leucinyl ethyl ether, (B) N-4-(2-methylimidazo[4,5-c]pyridin-1-yl)propylsulphonyl-L-leucinyl ethyl ether and (C) N-4-(2-methyl-imidazo[4,5-c]pyridin-5-yl)propylsulphonyl-L-leucinyl ethyl ether (a) L-Leucinyl ethyl ether Sodium hydride (60% dispersion in oil: 4.5 g, 0.11 mol) was added to a stirred solution of L-leucinol (12.8 ml, 0.10 mol) in a mixture of dry acetonitrile (24 ml) and dry THF (200 ml) at room temperature under argon. The mixture was heated at reflux for 2 h, cooled to 55° C. and ethyl iodide (8.2 ml, 0.10 mol) added carefully. The reaction mixture was heated at reflux overnight and allowed to cool to room temperature. Ice cold brine (100 ml) was added carefully and the mixture extracted with ethyl acetate (3×100 ml). The combined organic extracts were dried over anhydrous sodium sulphate, filtered and evaporated. The residue was distilled under reduced pressure to give L-leucinyl ethyl ether (4.5 g, 30%) as a colourless oil which was used directly in the next step.

delta$_H$ 3.49–3.14 (4H, m), 3.08–2.81 (2H, m), 1.73–1.50 (1H, m), 1.16–0.91 (6H, m), 0.84 (3H, d, J 6.9 Hz), 0.81 (3H, d, J 6.7 Hz).

(b) (A) N-4-(2-Methylimidazo[4,5-c]pyridin-3-yl)propylsulphonyl-L-leucinyl ethyl ether, (B) N-4-(2-methylimidazo[4,5-c]pyridin-1-yl)propylsulphonyl-L-leucinyl ethyl ether and (C) N-4-(2-methylimidazo[4,5-c]pyridin-5-yl)propylsulphonyl-L-leucinyl ethyl ether The three regioisomers were prepared by the procedure of Example 11, employing L-leucinyl ethyl ether and 3-chloropropylsulphonyl chloride as starting materials, and were separated by chromatography.

(A) N-4-(2-Methylimidazo[4,5-c]pyridin-3-yl)propylsulphonyl-L-leucinyl ethyl ether

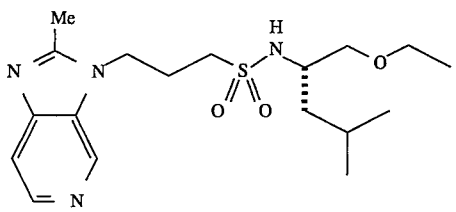

Yellow oil (1% yield for last step after chromatography (silica 4% methanol in DCM)): Analysis calculated for C$_{18}$H$_{30}$N$_4$O$_3$S.0.7 H$_2$O Requires C 54.72 H 8.01 N 14.18 Found C 54.72 H 7.91 N 13.87 i.r. (CDCl$_3$) 3395, 2960, 2210, 1610, 1400, 1115 cm$^{-1}$ delta$_H$ (CDCl$_3$) 8.71 (1H, s), 8.30 (1H, d, J 5.6 Hz), 7.50 (1H, d, J 5.4 Hz), 6.08 (1H, d, J 8.7 Hz), 4.34 (2H, t, J 7.5 Hz), 3.61–3.22 (5H, m), 3.12 (2H, t, J 6.9 Hz), 2.58 (3H, s), 2.36–2.19 (2H, m), 1.77–1.60 (1H, m), 1.40–1.12 (2H, m), 1.03 (3H, t, J 6.9 Hz), 0.84 (3H, d, J 6.3 Hz), 0.81 (3H, d, J 6.4 Hz);

(B) N-4-(2-methylimidazo[4,5-c]pyridin-1-yl)propylsulphonyl-L-leucinyl ethyl ether

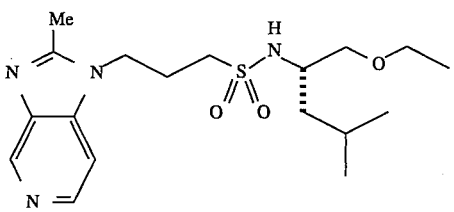

Colourles oil (1% yield): Analysis calculated for C$_{18}$H$_{30}$N$_4$O$_3$S Requires C 56.51 H 7.91 N 14.66 Found C 56.25 H 7.86 N 14.50 i.r. (CDCl$_3$) 2215, 1610, 1585, 1390, 1330, 1115 cm$^{-1}$ delta$_H$ 8.86 (1H, s), 8.23 (1H, d, J 5.5 Hz), 7.25 (1H, d, J 5.6 Hz), 6.26–6.11 (1H, m), 4.27 (2H, t, J 7.3 Hz), 3.63–3.24 (5H, m), 3.10 (2H, t, J 6.7 Hz), 2.57 (3H, s), 2.32–2.16 (2H, m), 1.80–1.62 (1H, m), 1.42–1.16 (2H, m), 1.07 (3H, t, J 7.0 Hz), 0.85 (3H, d, J 6.1 Hz), 0.82 (3H, d, J 6.2 Hz);

(C) N-4-(2-methylimidazo[4,5-c]pyridin-5-yl)propylsulphonyl-L-leucinyl ethyl ether

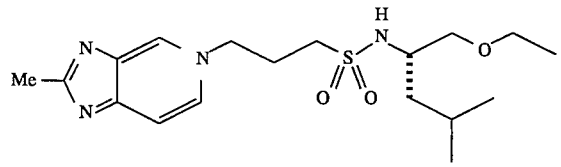

White crystalline solid (3% yield from ethyl acetate): m.p. 195° C. Analysis calculated for C$_{18}$H$_{30}$N$_4$O$_3$S Requires C 56.51 H 7.91 N 14.66 Found C 56.29 H 7.81 N 14.58 i.r. (CDCl$_3$) 2195, 1625, 1430, 1320, 1120 cm$^{-1}$ delta$_H$ (CDCl$_3$) 8.41 (1H, s), 7.60–7.49 (2H, m), 6.74–6.58 (1H, m), 4.55–4.40 (2H, m), 3.66–3.51 (1H, m), 3.48–3.26 (4H, m), 3.09 (2H, t, J 7.1 Hz), 2.69 (3H, s), 2.51–2.36 (2H, m), 1.80–1.63 (1H, m), 1.42–1.14 (2H, m), 1.06 (3H, t, J 7.0 Hz), 0.87 (3H, d, J 6.5 Hz), 0.82 (3H, d, J 6.6 Hz).

EXAMPLES 34–44

The compounds of Examples 34–44 may be prepared by the method of Example 33 employing the appropriate amino acid derivative in lieu of L-leucinyl ethyl ether as starting material.

34. N-4-(2-Methylimidazo[4,5-c]pyridin-1-yl)propylsulphonyl-L-leucinyl methyl ether
35. N-4-(2-Methylimidazo[4,5-c]pyridin-1-yl)propylsulphonyl-L-leucinyl octyl ether
36. N-4-(2-Methylimidazo[4,5-c]pyridin-1-yl)propylsulphonyl-L-leucinyl hexadecyl ether
37. N-4-(2-Methylimidazo[4,5-c]pyridin-1-yl)propylsulphonyl-L-leucinyl benzyl ether
38. N-4-(2-Methylimidazo[4,5-c]pyridin-1-yl)propyl sulphonyl-L-leucinyl propionate
39. N-4-(2-Methylimidazo[4,5-c]pyridin-1-yl)propylsulphonyl-L-leucinyl octadecanoate
40. N-4-(2-Methylimidazo[4,5-c]pyridin-1-yl)propylsulphonyl-L-leucinyl N'-ethyl carbamate
41. N-4-(2-Methylimidazo[4,5-c]pyridin-1-yl)propylsulphonyl-L-leucinyl N'-benzyl carbamate
42. N-4-(2-Methylimidazo[4,5-c]pyridin-1-yl)propylsulphonyl-L-leucinyl N'-2-pyridylcarbamate
43. N-4-(2-Methylimidazo[4,5-c]pyridin-1-yl)propylsulphonyl-L-leucinyl N-octadecylcarbamate
44. N-4-(2-Methylimidazo[4,5-c]pyridin-1-yl)propylsulphonyl-1-( 3-ethyl-1,2,4-oxadiazol- 5-yl)-3-methylbutylamine

EXAMPLE 45

(A) N-5-(2-Methylimidazo[4,5-c]pyridin-3-yl)pentanoyl-L-leucine ethyl ester and (B) N-5-(2-methylimidazo[4,5-c]pyridin-1-yl)pentanoyl-L-leucine ethyl ester The compounds of Example 45 were prepared by the procedure of Example 11, utilising 5-bromopentanoyl chloride in lieu of 4-bromobutanoyl chloride, and were separated by chromatography.

(A) N-5-(2-methylimidazo[4,5-c]pyridin-3-yl)pentanoyl-L-leucine ethyl ester

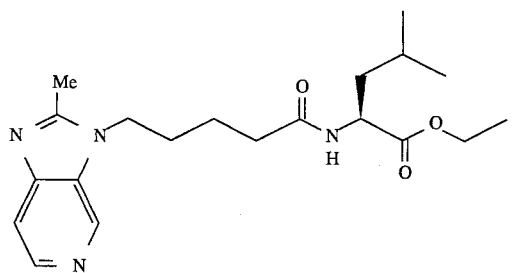

Colourless oil (8% yield for last step after chromatography (silica: 6% methanol in DCM)): i.r. (CDCl$_3$) 2210, 1730, 1670, 1500, 1400 cm$^{-1}$ delta$_H$ 8.62 (1H, s), 8.27 (1H, d, J 5.6 Hz), 7.46 (1H, d, J 5.1 Hz), 6.83 (1H, d, J 8.2 Hz), 4.54–4.43 (1H, m), 4.14–4.01 (4H, m), 2.52 (3H, s), 2.18 (2H, t, J 7.0 Hz), 1.86–1.35 (7H, m), 1.15 (3H, t, J 7.1 Hz), 0.81 (3H, d, J 5.9 Hz), 0.79 (3H, d, J 6.1 Hz); delta$_C$ 172.85, 171.82, 154.60, 147.28, 141.11, 132.50, 131.86, 113.32, 60.67, 50.39, 43.67, 40.56, 34.72, 28.83, 24.47, 22.34, 22.29, 21.27, 13.70, 13.37;

(B) N-5-(2-methylimidazo[4,5-c]pyridin-1-yl)pentanoyl-L-leucine ethyl ester

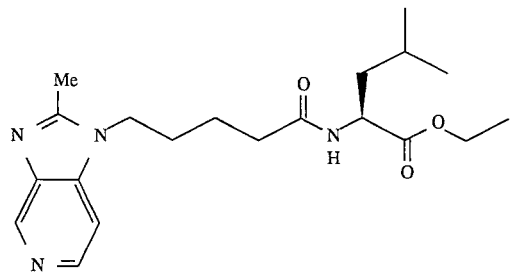

Colourless oil (4% yield): i.r. (CDCl$_3$) 2210, 1730, 1670, 1610, 1510 cm$^{-1}$ delta$_H$ 8.73 (1H, s), 8.12 (1H, d, J 5.5 Hz), 7.46 (1H, d, J 8.1 Hz), 7.07 (1H, d, J 5.5 Hz), 4.45–4.32 (1H, m), 4.03–3.85 (4H, m), 2.41 (3H, s), 2.18–2.05 (2H, m), 1.72–1.28 (7H, m), 1.04 (3H, t, J 7.1 Hz), 0.71 (3H, d, J 6.3 Hz), 0.67 (3H, d, J 6.4 Hz); delta$_C$ 172.72, 171.87, 153.04, 140.73, 140.67, 139.64, 139.29, 104.61, 60.59, 50.38, 43.40, 40.47, 34.66, 28.56, 24.42, 22.30, 21.21, 13.65, 13.32.

EXAMPLES 46–55

The compounds of Examples 46–55 may be prepared by the method of Example 11 employing the appropriate amino acid derivative in lieu of L-leucine ethyl ester hydrochloride as starting material and for certain compounds the appropriate substituted 4-bromopentanoyl chloride in lieu of 4-bromopentanoyl chloride.

46. N-5-(2-Methylimidazo[4,5-c]pyridin-1-yl)pentanoyl-L-leucine i-propyl ester
47. N-5-(2-Methylimidazo[4,5-c]pyridin-1-yl)pentanoyl-O-methyl-L-tyrosine ethyl ester
48. N-5-(2-Methylimidazo[4,5-c]pyridin-1-yl)pentanoyl-D, L-allylglycine ethyl ester
49. N-5-(2-Methylimidazo[4,5-c]pyridin-1-yl)pentanoyl-L-norleucine allyl ester 50. N-5-(2-Methylimidazo[4,5-c]pyridin-1-yl)-2-methylpentanoyl-L-leucinyl ethyl ether
51. N-5-(2-Methylimidazo[4,5-c]pyridin-1-yl)-2,2-dimethylpentanoyl-L-leucine 2-benzoxyethylethyl ester
52. N-5-(2-Methylimidazo[4,5-c]pyridin-1-yl)-3-hydroxypentanoyl-L-leucine 2-( 2-ethoxyethoxy)ethyl ester
53. N-5-(2-Methylimidazo[4,5-c]pyridin-1-yl)pentanoyl-1-( 3-methyl-1,2,4-oxadiazol- 5-yl)-3-methylbutylamine
54. N-5-(2-Methylimidazo[4,5-c]pyridin-1-yl)pentanoyl-1-(6-ethylpyrazin-2-yl)- 3-methylbutylamine
55. N-5-(2-Methylimidazo[4,5-c]pyridin-1-yl)pentanoyl-L-leucinyl N'-ethylcarbamate

EXAMPLE 56

(A) N-Methyl-N-6-(2-methylimidazo[4,5-c]pyridin-3-yl)hexanoyl-L-leucine ethyl ester, (B) N-methyl-N-6-(2-methylimidazo[4,5-c]pyridin-1-yl)hexanoyl-L-leucine ethyl ester and (C) N-methyl-N-6-(2-methylimidazo[4,5-c]pyridin-5-yl)hexanoyl-L-leucine ethyl ester (a) N-Methyl-N-6-bromohexanoyl-L-leucine ethyl ester Sodium hydride (60% dispersion in oil; 2.0 g, 50 mmol) was added to a stirred solution of N-6-bromohexanoyl-L-leucine ethyl ester (15.0 g, 45 mmol) in anhydrous THF (150 ml) at 0° C. After the effervesence had ceased methyl iodide (8.4 ml) was added. The reaction mixture was allowed to warm up to room temperature and was stirred overnight. The solvent was removed under reduced pressure and the residue taken up in ethyl acetate, washed with brine, dried over anhydrous sodium sulphate, filtered and concentrated to give crude N-methyl-N- 6-bromohexanoyl-L-leucine ethyl ester (14.0 g, 89%) as a pale yellow oil which was used directly in the next step.

delta$_H$ 5.31 (1H, dd, J 10.0, 5.7 Hz), 4.20–4.04 (2H, m), 3.39 (2H, t, J 6.7 Hz), 2.89 (2.5H, s), 2.80 (0.5H, s), 2.41–2.28 (2H, m), 1.95–1.56 (6H, m), 1.54–1.36 (3H, m), 1.23 (3H, t, J 7.1 Hz), 0.92 (3H, d, J 6.2 Hz), 0.89 (3H, d, J 6.1 Hz).

(b) (A) N-Methyl-N-6-(2-methylimidazo[4,5-c]pyridin-3-yl)hex-anoyl-L-leucine ethyl ester, (B) N-methyl-N-6-(2-methylimidazo-[4,5-c]pyridin-1-yl)hexanoyl-L-leucine ethyl ester and (C) N-methyl-N-6-(2-methylimidazo[4,5-c]pyridin-5-yl)hexanoyl-L-leucine ethyl ester The three regioisomers were prepared by the procedure of Example 11 Step (b), employing N-methyl-N-6-bromohexanoyl-L-leucine ethyl ester in lieu of N-3-bromopropanoyl-L-leucine ethyl ester, and were separated by chromatography.

(A) N-methyl-N-6-(2-methylimidazo[4,5-c]pyridin-3-yl)-hexanoyl-L-leucine ethyl ester

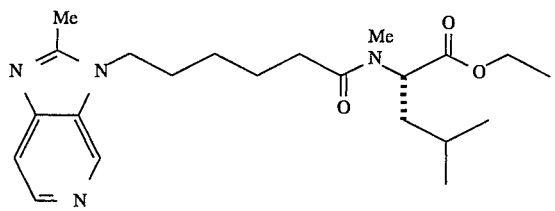

Yellow oil (5% yield for last step after chromatography (silica: 6% methanol in DCM)): i.r. (CDCl$_3$) 2210, 1725, 1630, 1400, 1195 cm$^{-1}$ delta$_H$ 8.71 (1H, s), 8.38 (1H, d, J 5.5 Hz), 7.57 (1H, d, J 5.4 Hz), 5.33–5.27 (1H, m), 4.20–4.06 (4H, m), 2.86 (3H, s), 2.62 (3H, s), 2.49–2.26 (2H, m), 1.95–1.80 (2H, m), 1.79–1.62 (4H, m), 1.49–1.32 (3H, m), 1.23 (3H, t, J 7.1 Hz), 0.92 (3H, d, J 6.9 Hz), 0.89 (3H, d, J 6.8 Hz); delta$_C$ 173.13, 171.98, 154.82, 141.70, 132.25, 113.84, 60.97, 54.18, 44.16, 37.28, 33.05, 31.17, 29.79, 26.51, 25.01, 24.28, 23.16, 21.34, 14.14;

(B) N-methyl-N-6-(2-methylimidazo[4,5-c]pyridin-1-yl)-hexanoyl-L-leucine ethyl ester

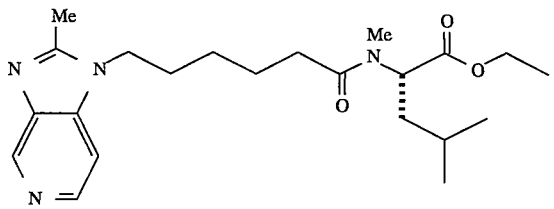

Yellow oil (6% yield): i.r. (CDCl$_3$) 2210, 1725, 1630, 1610, 1395, 1025 cm$^{-1}$ delta$_H$ 8.94 (1H, s), 8.35 (1H, d, J 5.6 Hz), 7.23 (1H, d, J 4.9 Hz), 5.32–5.27 (1H, m), 4.18–4.07 (4H, m), 2.86 (3H, s), 2.61 (3H, s), 2.48–2.26 (2H, m), 1.87–1.63 (6H, m), 1.59–1.31 (3H, m), 1.22 (3H, t, J 7.1 Hz), 0.94–0.87 (6H, m); delta$_C$ 172.91, 171.63, 152.99, 141.14, 141.08, 139.76, 139.45, 104.55, 60.66, 53.95, 43.60, 36.96, 32.74, 30.95, 29.25, 26.16, 24.69, 23.97, 22.88, 21.03, 13.83, 13.58;

(C) N-methyl-N-6-(2-methylimidazo[4,5-c]pyridin-5-yl)-hexanoyl-L-leucine ethyl ester

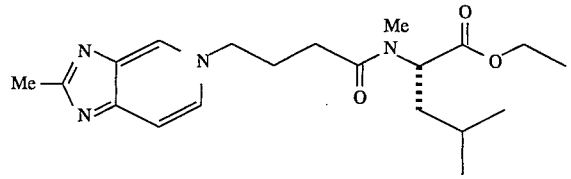

Colourless oil (17% yield): i.r. (CDCl$_3$) 2200, 1730, 1630, 1435, 1320 cm$^{-1}$ delta$_H$ 8.31 (1H, s), 7.62 (1H, d, J 6.7 Hz), 7.43 (1H, d, J 6.7 Hz), 5.01–4.94 (1H, m), 4.13 (2H, t, J 7.0 Hz), 3.86–3.76 (2H, m), 2.58 (3H, s), 2.43 (3H, s), 2.07–1.99 (2H, m), 1.78–1.61 (2H, m), 1.50–1.30 (4H, m), 1.11–1.10 (3H, m), 0.92 (3H, t, J 7.1 Hz), 0.62 (3H, d, J 6.6 Hz), 0.58 (3H, d, J 6.5 Hz); delta$_C$ 172.48, 171.20, 153.72, 143.25, 130.37, 129.09, 111.30, 60.28, 59.06, 53.65, 36.59, 32.30, 30.86, 30.62, 25.08, 24.28, 23.25, 22.51, 20.69, 17.06.

EXAMPLE 57

(A) N-Methyl-N-6-(2-methylimidazo[4,5-c]pyridin-3-yl)hexanoyl-L-isoleucine allyl ester, (B) N-methyl-N-6-(2-methylimidazo[4,5-c]pyridin-1-yl)hexanoyl-L-isoleucine allyl ester and (C) N-methyl-N-6-(2-methylimidazo[4,5-c]pyridin-5-yl)hexanoyl-L-isoleucine allyl ester The compounds of Example 57 were prepared by the methods of Example 1 Step (a) and Example 56 utilising L-isoleucine allyl ester hydrochloride in lieu of L-leucine ethyl ester hydrochloride as starting material, and were separated by chromatography.

(A) N-methyl-N-6-(2-methylimidazo[4,5-c]pyridin-3-yl)-hexanoyl-L-isoleucine allyl ester

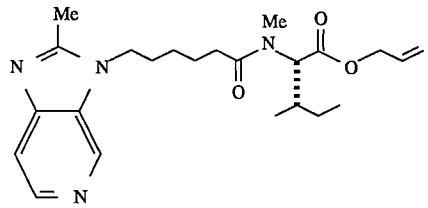

Yellow oil (4% yield for last step after chromatography (silica: 6% methanol in DCM)): i.r. (CDCl$_3$) 2210, 1730, 1630, 1400, 1180 cm$^{-1}$ delta$_H$ 8.72 (1H, s), 8.39 (1H, d, J 5.6 Hz), 7.57 (1H, d, J 5.7 Hz), 5.93–5.80 (1H, m), 5.33–5.17 (2H, m), 5.08–5.00 (1H, m), 4.61–4.56 (2H, m), 4.18 (2H, t, J 7.2 Hz), 2.93 (3H, s), 2.63 (3H, s), 2.33 (2H, t, J 7.1 Hz), 2.10–1.81 (3H, m), 1.79–1.63 (2H, m), 1.50–1.04 (4H, m), 0.98–0.76 (6H, m); delta$_C$ 172.54, 170.38, 154.26, 147.21, 141.26, 135.51, 131.94, 131.34, 117.87, 113.25, 64.66, 59.54, 43.64, 32.98, 32.64, 30.86, 29.30, 26.04, 24.63, 23.82, 15.27, 13.43, 10.17;

(B) N-methyl-N-6-(2-methylimidazo[4,5-c]pyridin-1-yl)-hexanoyl-L-isoleucine allyl ester

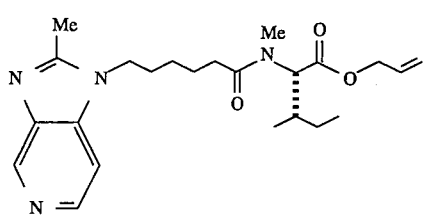

Yellow oil (2% yield): i.r. (CDCl$_3$) 2210, 1730, 1635, 1395, 1160 cm$^{-1}$ delta$_H$ 8.78 (1H, s), 8.18 (1H, d, J 5.5 Hz), 7.07 (1H, d, J 5.4 Hz), 5.79–5.62 (1H, m), 5.16–5.00 (2H, m), 4.93–4.82 (1H, m), 4.47–4.36 (2H, m), 4.00–3.86 (2H, m), 2.78 (3H, s), 2.44 (3H, s), 2.17 (2H, t, J 7.0 Hz), 1.95–1.75 (1H, m), 1.73–1.45 (4H, m), 1.34–1.10 (4H, m), 0.82–0.59 (6H, m); delta$_C$ 172.60, 170.41,152.78, 141.02, 140.95, 139.58, 139.36, 131.34, 117.90, 104.37, 64.69, 59.60, 43.40, 33.02, 32.64, 29.09, 26.01, 24.66, 23.81, 15.30, 15.25, 10.20;

(C) N-methyl-N-6-(2-methylimidazo[4,5-c]pyridin-5-yl)-hexanoyl-L-isoleucine allyl ester

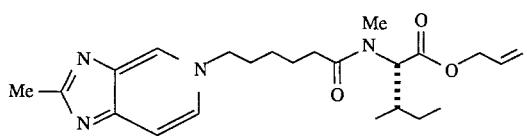

Yellow oil (8% yield): i.r. (CDCl$_3$) 2200, 1730, 1630, 1315, 1125 cm$^{-1}$ delta$_H$ (250 MHz, CDCl3); 8.27 (1H, s), 7.57 (2H, s), 5.89–5.76 (1H, m), 5.28–5.14 (2H, m), 5.04–4.97 (1H, m), 4.59–4.52 (2H, m), 4.27 (2H, t, J 7.1 Hz), 3.44 (3H, s), 2.70 (3H, s), 2.28 (2H, t, J 7.0 Hz), 2.03 (3H, m), 1.74–1.60 (2H, m), 1.41–1.21 (4H, m), 0.97–0.72 (6H, m); delta$_C$ 174.45, 172.89, 156.01, 145.14, 131.59, 129.32, 128.43, 110.92, 118.35, 111.65, 65.10, 59.97, 59.30, 33.36, 32.84, 31.30, 25.63, 25.00, 23.69, 18.06, 15.55, 10.51.

EXAMPLE 58

(A) N-Methyl-N-6-(2-methylimidazo[4,5-c]pyridin-3-yl)hexanoyl-L-leucinyl ethyl ether, (B) N-methyl-N-6-(2-methylimidazo[4,5-c]pyridin-1-yl)hexanoyl-L-leucinyl ethyl ether and (C) N-methyl-N-6-(2-methylimidazo[4,5-c]pyridin-5-yl)hexanoyl-L-leucinyl ethyl ether The compounds of Example 58 were prepared by the methods of Example 1 Step (a) and Example 56 utilising L-leucinyl ethyl ether in lieu of L-leucine ethyl ester hydrochloride as starting material, and were separated by chromatography.

(A) N-Methyl-N-6-(2-methylimidazo[4,5-c]pyridin-3-yl)-hexanoyl-L-leucinyl ethyl ether

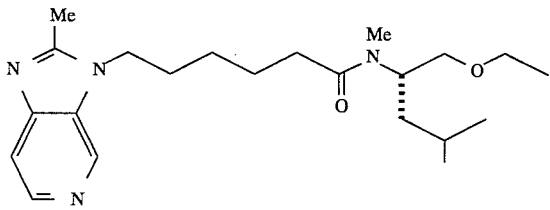

Pale yellow oil (2% yield for last step after chromatography (silica: 5% methanol in DCM)): i.r. (CDCl$_3$) 2210, 1625, 1400, 1120 cm$^{-1}$ delta$_H$ 8.60 (1H, s), 8.27 (1H, d, J 5.6 Hz), 7.44 (1H, d, J 5.9 Hz), 4.84–4.71 (0.5H, m), 4.06 (2H, t, J 7.3 Hz), 3.90–3.79 (0.5H, m), 3.42–3.17 (4H, m), 2.68 (1.5H, s), 2.62 (1.5H, s), 2.50 (3H, s), 2.23–2.12 (2H, m), 1.82–1.67 (2H, m), 1.64–1.51 (2H, m), 1.40–1.20 (4H, m), 1.15–0.92 (4H, m), 0.81–0.71 (6H, m); delta$_C$ 173.02, 172.46, 154.47, 147.43, 141.47, 132.70, 132.11,113.47, 70.87, 70.55, 66.36, 65.82, 54.34, 49.55, 43.91, 37.90, 37.07, 33.15, 32.29, 29.54, 26.38, 26.29, 26.19, 24.31, 24.23, 24.16, 23.04, 22.97, 22.02, 21.81, 14.86, 14.80, 13.64;

(B) N-methyl-N-6-(2-methylimidazo[4,5-c]pyridin-1-yl)-hexanoyl-L-leucinyl ethyl ether

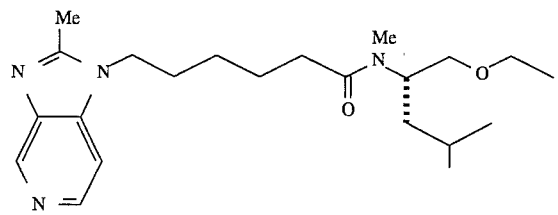

Pale yellow oil (1% yield): i.r. (CDCl$_3$) 2210, 1620, 1395, 1120 cm$^{-1}$ delta$_H$ 8.91 (1H, s), 8.31 (1H, d, J 5.6 Hz), 7.20 (1H, d, J 5.7 Hz), 4.91–4.78 (0.5H, m), 4.06 (2H, t, J 7.3 Hz), 3.98–3.87 (0.5H, m), 3.49–3.23 (4H, m), 2.76 (1.5H, s), 2.70 (1.5H, s), 2.57 (3H, s), 2.51–2.39 (0.5H, m), 2.32–2.18 (1.5H m), 1.84–1.59 (4H, m), 1.48–1.28 (4H, m), 1.23–1.28 (4H, m), 0.90–0.80 (6H, m); delta$_C$ 173.23, 172.66, 153.06, 141.52, 141.36, 139.91, 139.67, 104.65, 71.01, 70.71, 66.54, 65.98, 54.52, 49.73, 43.79, 38.06, 37.22, 33.31, 32.43, 29.48, 26.47, 26.41, 24.84, 24.43, 24.28, 23.19, 23.11, 22.16, 21.96, 15.02, 14.95, 13.79;

(C) N-methyl-N-6-(2-methylimidazo[4,5-c]pyridin-5-yl)-hexanoyl-L-leucinyl ethyl ether

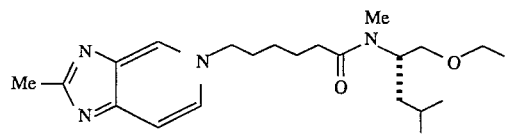

Brown oil (9% yield): i.r. (CDCl$_3$) 2195, 1625, 1430, 1120 cm$^{-1}$ delta$_H$ 8.29 (1H, s), 7.63–7.57 (1H, m), 7.54–7.51 (1H, m), 4.88–4.72 (1H, m), 4.26 (2H, t, J 7.1 Hz), 3.45–3.20 (4H, m), 2.71 (3H, s), 2.65 (3H, s), 2.28–2.15 (2H, m), 1.97–1.82 (2H, m), 1.71–1.55 (2H, m), 1.45–1.17 (5H, m), 1.15–0.95 (3H, m), 0.85–0.75 (6H, m); delta$_C$ 173.45, 173.36, 172.63, 172.11, 155.27, 144.65, 144.59, 129.40, 129.32, 128.26, 111.10, 70.51, 70.17, 66.01, 65.51, 58.95, 53.99, 49.31, 37.54, 36.75, 32.73, 31.83, 30.96, 29.05, 25.91, 25.35, 25.25, 24.32, 23.93, 23.63, 23.40, 22.73, 22.64, 21.72, 21.50, 17.67.

EXAMPLES 59–86

The compounds of Examples 59–86 may be prepared by the method of Example 58 employing the appropriate amino acid derivative in lieu of L-leucinyl ethyl ether as starting material and for certain compounds the appropriate substituted haloalkanoyl or haloalkylsulphonylchloride in lieu of 6-bromohexanoyl chloride.

59. N-Methyl-N-6-(2-methylimidazo[4,5-c]pyridin-1-yl)-hexanoyl-L-leucinyl hexadecyl ether
60. N-Methyl-N-6-(2-methylimidazo[4,5-c]pyridin-1-yl)-hexanoyl-L-phenyl-alaninyl ethyl ether
61. N-Methyl-N-6-(2-methylimidazo[4,5-c]pyridin-1-yl)-hexanoyl-L-leucinyl 4-methoxybenzyl ether
62. N-Methyl-N-6-(2-methylimidazo[4,5-c]pyridin-1-yl)-hexanoyl-L-norleucinyl ethyl ether
63. N-Methyl-N-6-(2-methylimidazo[4,5-c]pyridin-1-yl)-hexanoyl-O-benzyl-L-serinyl ethyl ether
64. N-Methyl-N-6-(2-methylimidazo[4,5-c]pyridin-1-yl)-2-methylhexanoyl-L-leucinyl ethyl ether
65. N-Ethoxycarbonyl-N-6-(2-methylimidazo[4,5-c]pyridin-1-yl)hexanoyl-L-leucinyl ethyl ether
66. N-Methyl-N-6-(2-methylimidazo[4,5-c]pyridin-1-yl)-5-methoxyhexanoyl-L-leucinyl ethyl ether
67. N-Methyl-N-6-(2-methylimidazo[4,5-c]pyridin-1-yl)-hexanoyl-1-(3-ethyl- 1,2,4-oxadiazol-5-yl)-3-methylbutylamine 68. N-Methyl-N-4-(2-methylimidazo[4,5-c]pyridin-1-yl)butanoyl-L-leucine ethyl ester
69. N-Allyl-N-4-(2-methylimidazo[4,5-c]pyridin-1-yl)butanoyl-L-leucine i-propyl ester
70. N-Methyl-N-4-(2-methylimidazo[4,5-c]pyridin-1-yl)butanoyl-L-leucinyl ethyl ether
71. N-Methyl-N-4-(2-methylimidazo[4,5-c]pyridin-1-yl)-2-methylbutanoyl-L-leucinyl ethyl ether
72. N-Methyl-N-5-(2-methylimidazo[4,5-c]pyridin-1-yl)-pentanoyl-L-leucine ethyl ester
73. N-Methyl-N-5-(2-methylimidazo[4,5-c]pyridin-1-yl)-pentanoyl-L-leucinyl ethyl ether
74. N-Methyl-N-5-(2-methylimidazo[4,5-c]pyridin-1-yl)-2-methylpentanoyl-L-leucinyl ethyl ether
75. N-Methyl-N-5-(2-methylimidazo[4,5-c]pyridin-1-yl)-pentanoyl-L-leucinyl hexadecyl ether
76. N-Methyl-N-3-(2-methylimidazo[4,5-c]pyridin-1-yl)-propylsulphonyl-L-leucine ethyl ester
77. N-Methyl-N-3-(2-methylimidazo[4,5-c]pyridin-1-yl)-propylsulphonyl-L-leucine i-propyl ester
78. N-Methyl-N-3-(2-methylimidazo[4,5-c]pyridin-1-yl)-propylsulphonyl-L-leucinyl ethyl ether
79. N-Methyl-N-3-(2-methylimidazo[4,5-c]pyridin-1-yl)-propylsulphonyl-L-leucinyl hexadecyl ester
80. N-Methyl-N-3-(2-methylimidazo[4,5-c]pyridin-1-yl)-propylsulphonyl-1-(3-ethyl- 1,2,4-oxadiazol-5-yl)-3-methylbutylamine
81. N-Methyl-N-4-(2-methylimidazo[4,5-c]pyridin-1-yl)butylsulphonyl-L-leucine ethyl ester
82. N-Methyl-N-4-(2-methylimidazo[4,5-c]pyridin-1-yl)butylsulphonyl-L-leucinyl ethyl ether
83. N-Methyl-N-4-(2-methylimidazo[4,5-c]pyridin-1-yl)butylsulphonyl-L-leucinyl heptadecyl ether
84. N-Methyl-N-5-(2-methylimidazo[4,5-c]pyridin-1-yl)-pentylsulphonyl-L-leucine ethyl ester
85. N-Methyl-N-5-(2-methylimidazo[4,5-c]pyridin-1-yl)-pentylsulphonyl-L-leucine i-propyl ester
86. N-Methyl-N-5-(2-methylimidazo[4,5-c]pyridin-1-yl)-pentylsulphonyl-L-leucinyl ethyl ether

EXAMPLE 87

(A) N-8-(2-Methylimidazo[4,5-c]pyridin-3-yl)octanoyl-L-leucine ethyl ester, (B) N-8-(2-methylimidazo[4,5-c]pyridin-1-yl)octanoyl-L-leucine ethyl ester and (C) N-8-(2-methylimidazo[4,5-c]pyridin-5-yl)octanoyl-L-leucine ethyl ester The compounds of Example 87 were prepared by the procedure of Example 11 utilising pentafluorophenyl-8-bromooctanoate in lieu of 4-bromobutanoyl chloride, and were separated by chromatography.

(A) N-8-(2-methylimidazo[4,5-c]pyridin-3-yl)octanoyl-L-leucine ethyl ester

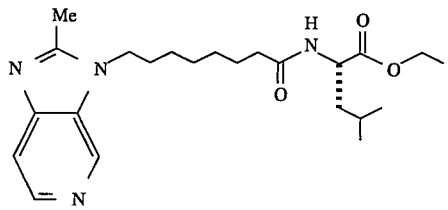

Colourless oil (7% yield for last step after chromatography (silica: 6% methanol in DCM)): i.r. (CDCl$_3$) 2210, 1730, 1665, 1500, 1400 cm$^{-1}$ delta$_H$ 8.58 (1H, s), 8.24, (1H, d, J 5.5 Hz), 7.43 (1H, d, 5.3 Hz), 6.68 (1H, d, J 8.2 Hz), 4.51–4.40 (1H, m), 4.06–3.95 (4H, m), 2.49 (3H, s), 2.06 (2H, t, J 7.4 Hz), 1.76–1.60 (2H, m), 1.58–1.34 (5H, m), 1.27–1.10 (6H, m), 1.11 (3H, t, J 7.4 Hz), 0.78 (3H, d, J 5.7 Hz), 0.76 (3H, d, J 5.7 Hz); delta$_C$ 172.98, 172.54, 154.50, 147.37, 141.33, 132.66, 132.03, 113.44, 60.75, 50.32, 43.94, 41.00, 35.73, 29.44, 28.51, 26.25, 25.00, 24.53, 22.46, 21.50, 13.79, 13.54;

(B) N-8-(2-methylimidazo[4,5-c]pyridin-1-yl)octanoyl-L-leucine ethyl ester

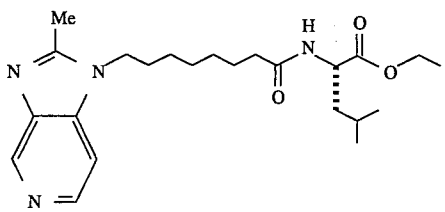

Colourless oil (8% yield): i.r. (CDCl$_3$) 2210, 1730, 1670, 1500 cm$^{-1}$ delta$_H$ 8.78 (1H, s), 8.19 (1H, d, J 5.5 Hz), 7.08 (1H, d, J 5.5 Hz), 6.90 (1H, d, J 8.2 Hz), 4.51–4.38 (1H, m), 4.05–3.83 (4H, m), 2.45 (3H, s), 2.06 (2H, t, J 7.3 Hz), 1.67–1.30 (7H, m), 1.23–1.07 (6H, m), 1.08 (3H, t, J 7.1 Hz), 0.75 (3H, d, J 5.9 Hz), 0.73 (3H, d, J 6.0 Hz); delta$_C$ 172.89, 172.60, 152.96, 140.96, 139.70, 139.40, 104.54, 60.66, 50.30, 43.66, 40.88, 35.64, 29.18, 28.44, 26.19, 24.97, 24.47, 22.41, 21.43, 13.74, 13.48;

(C) N-8-(2-methylimidazo[4,5-c]pyridin-5-yl)octanoyl-L-leucine ethyl ester

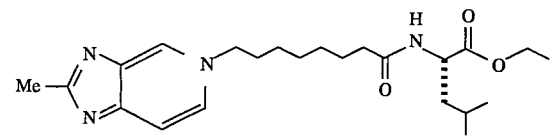

Colourless oil (7% yield): i.r. (CDCl$_3$) 2200, 1730, 1665, 1500, 1435 cm$^{-1}$ delta$_H$ 8.30 (1H, s), 7.50–7.48 (2H, m), 7.08 (1H, d, J 8.1 Hz), 4.52–4.41 (1H, m), 4.15 (2H, t, J 7.3 Hz), 4.04 (2H, q, J 7.1 Hz), 2.61 (3H, s), 2.06 (2H, t, J 7.3 Hz), 1.87–1.73 (2H, m), 1.65–1.40 (5H, m), 1.23–1.10 (9H, m), 0.80 (3H, d, J 6.4 Hz), 0.78 (3H, d, J 6.5 Hz); delta$_C$ 174.39, 173.23, 172.72, 150.04, 145.21, 129.09, 128.37, 111.50, 60.81, 59.44, 50.51, 40.88, 35.62, 31.78, 31.28, 28.40, 28.23, 25.63, 24.95, 24.62, 22.53, 21.50, 18.06, 13.86.

EXAMPLES 88–96

The compounds of Examples 88–96 may be prepared by the method of Example 11 or Example 56 employing the appropriate amino acid derivative and the appropriate substituted haloalkanoyl chloride as starting materials.

88. N-8-(2-Methylimidazo[4,5-c]pyridin-1-yl)-2-methyloctanoyl-L-leucine ethyl ester
89. N-8-(2-Methylimidazo[4,5-c]pyridin-1-yl)-2,2-dimethyloctanoyl-L-phenylalanine ethyl ester
90. N-Methyl-N-8-(2-methylimidazo[4,5-c]pyridin-1-yl)octanoyl-L-leucine i-propyl ester
91. N-Methyl-N-8-(2-methylimidazo[4,5-c]pyridin-1-yl)octanoyl-L-leucinyl ethyl ether
92. N-Methyl-N-8-(2-methylimidazo[4,5-c]pyridin-1-yl)octanoyl-1-( 3-ethyl-1,2,4-oxadiazol- 5-yl)-3-methylbutylamine
93. N-7-(2-Methylimidazo[4,5-c]pyridin-1-yl)heptanoyl-L-leucine ethyl ester 94. N-Methyl-N-7-(2-methylimidazo[4,5-c]pyridin-1-yl)-heptanoyl-L-leucinyl ethyl ether
95. N-Methyl-N-7-(2-methylimidazo[4,5-c]pyridin-1-yl)-2,2-dimethylheptanoyl-L-leucinyl ethyl ether
96. N-Methyl-N-7-(2-methylimidazo[4,5-c]pyridin-1-yl)-heptanoyl-L-leucinyl N'-hexadecylcarbamate

EXAMPLE 97

N-11-(2-Methylbenzimidazol-1-yl)undecanoyl-L-leucine ethyl ester

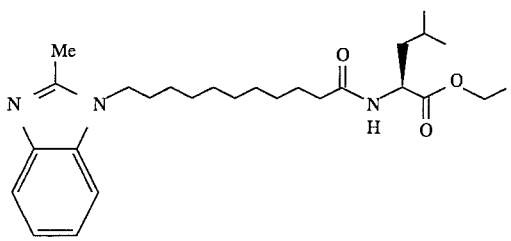

N-11-(2-Methylbenzimidazol-1-yl)undecanoyl-L-leucine ethyl ester was prepared by the procedure of Example 1 utilising pentafluorophenyl-11-bromoundecanoate in lieu of 6-bromohexanoyl chloride and 2-methylbenzimidazole in lieu of 2-methylimidazo[4,5-c]pyridine.

Colourless oil (30% yield for last step after chromatography (silica: 4% methanol in DCM)): i.r. (CDCl$_3$) 2200, 1730, 1665, 1500, 1400 cm$^{-1}$ delta$_H$ 7.63–7.58 (1H, m), 7.23–7.11 (3H, m), 6.42 (1H, d, J 7.7 Hz), 4.61–4.52 (1H, m), 4.11 (2H, q, J 6.7 Hz), 3.99 (2H, t, J 7.3 Hz), 2.52 (3H, s), 2.14 (2H, t, J 7.5 Hz), 1.79–1.40 (7H, m), 1.34–1.05 (15H, m), 0.88 (3H, d, J 5.3 Hz), 0.86 (3H, d, J 5.3 Hz); delta$_C$ 173.04, 172.76, 151.12, 142.33, 134.85, 121.61, 121.39, 118.64, 108.94, 60.88, 53.22, 50.41, 43.57, 41.29, 36.12, 29.44, 29.01, 28.93, 26.60, 25.31, 24.63, 24.38, 22.56, 21.69, 13.89, 13.61.

EXAMPLE 98

(A) N-11-(2-Methylimidazo[4,5-c]pyridin-3-yl)undecanoyl-L-leucine ethyl ester and (B) N-11-(2-methylimidazo[4,5-c]pyridin-1-yl)undecanoyl-L-leucine ethyl ester The compounds of Example 98 were prepared by the procedure of Example 11 utilising pentafluorophenyl-11-bromoundecanoate in lieu of 4-bromobutanoyl chloride, and were separated by chromatography.

(A) N-10-(2-Methylimidazo[4,5-c]pyridin-3-yl)undecanoyl-L-leucine ethyl ester

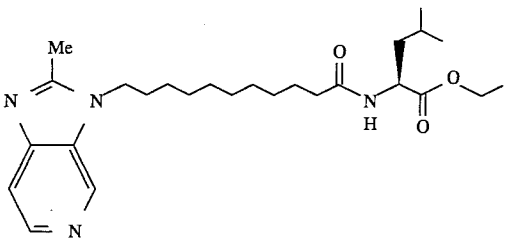

Colourless oil (5% yield for last step after chromatography (silica: 5% methanol in DCM)): i.r. (CDCl$_3$) 1730, 1665 cm$^{-1}$ delta$_H$ 8.66 (1H, br s), 8.32 (1H, br s), 7.50 (1H, d, J 5.3 Hz), 6.47 (1H, d, J 8.3 Hz), 4.60–4.50 (1H, m), 4.16–4.02 (4H, m), 2.57 (3H, s), 2.14 (2H, t, J 7.3 Hz), 1.82–1.69 (2H, m), 1.68–1.40 (5H, m), 1.36–1.10 (15H, m), 0.85 (3H, d, J 6.1 Hz), 0.84 (3H, d, J 6.2 Hz); delta$_C$ 173.12, 172.81, 154.62, 147.56, 141.50, 132.84, 132.15, 113.62, 60.93, 50.42, 44.13, 41.35, 36.21, 29.60, 28.95, 28.83, 26.51, 25.34, 24.68, 22.61, 21.71, 13.93, 13.73;

(B) N-11-(2-methylimidazo[4,5-c]pyridin-1-yl)undecanoyl-L-leucine ethyl ester

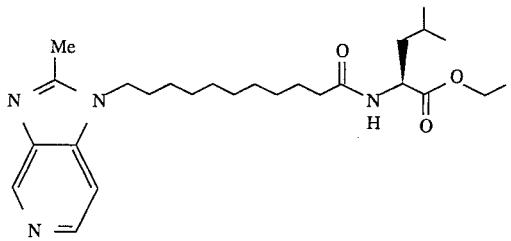

Colourless oil (5% yield): i.r. (CDCl$_3$) 1730, 1670 cm$^{-1}$ delta$_H$ (CDCl$_3$)cm$^{-1}$ 8.93 (1H, br s), 8.34 (1H, br s), 7.20 (1H, d, J 5.3 Hz), 6.20 (1H, d, J 8.3 Hz), 4.64–4.53 (1H, m), 4.13 (2H, q, J 7.1 Hz), 4.06 (2H, t, J 7.4 Hz), 2.59 (3H, s), 2.16 (2H, t, J 7.3 Hz), 1.80–1.64 (2H, m), 1.66–1.41 (5H, m), 1.34–1.14 (15H, m), 0.90 (3H, d, J 6.0 Hz), 0.89 (3H, d, J 6.2 Hz); delta$_C$ 173.19, 172.78, 153.16, 141.51, 141.33, 140.01, 104.73, 61.09, 50.51, 44.03, 41.58, 36.34, 29.55, 29.12, 29.03, 28.98, 26.69, 25.41, 24.78, 22.68, 21.87, 14.01, 13.82.

EXAMPLES 99–109

The compounds of Examples 99–109 may be prepared by the method of Example 11 or Example 56 employing the appropriate amino acid derivative and the appropriate substituted haloalkanoyl chloride or pentafluorophenyl haloalkanoate as starting materials.

99. N-9-(2-Methylimidazo[4,5-c]pyridin-1-yl)nonanoyl-L-leucine ethyl ester
100. N-Methyl-N-9-(2-methylimidazo[4,5-c]pyridin-1-yl)-nonanoyl-L-leucine i-propyl ester
101. N-Methyl-N-9-(2-methylimidazo[4,5-c]pyridin-1-yl)-nonanoyl-L-leucinyl ethyl ether
102. N-Methyl-N-9-(2-methylimidazo[4,5-c]pyridin-1-yl)-2,2-dimethylnonanoyl-L-leucinyl ethyl ether
103. N-Methyl-N-10-(2-methylimidazo[4,5-c]pyridin-1-yl)-decanoyl-L-leucinyl ethyl ester
104. N-Methyl-N-10-(2-methylimidazo[4,5-c]pyridin-1-yl)-decanoyl-L-leucine ethyl ester
105. N-Methyl-N-11-(2-methylimidazo[4,5-c]pyridin-1-yl)undecanoyl-L-leucine ethyl ester
106. N-Methyl-N-11-(2-methylimidazo[4,5-c]pyridin-1-yl)undecanoyl-L-leucinyl ethyl ether
107. N-Methyl-N-12-(2-methylimidazo[4,5-c]pyridin-1-yl)-dodecanoyl-L-leucinyl ethyl ether
108. N-Methyl-N-6-(2-methylimidazo[4,5-c]pyridin-1-yl)-hexanoyl-D-leucine ethyl ester
109. N-Methyl-N-6-(2-methylimidazo[4,5-c]pyridin-1-yl)-hexanoyl-L-phenylalanine ethyl ester

EXAMPLE 110

N-Methyl-N-6-(2-methylimidazo[4,5-c]pyridin-1-yl)hexanoyl-L-leucine

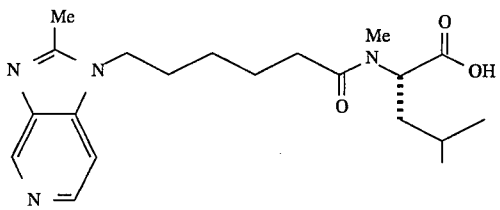

2M Potassium hydroxide (2.5 ml) was added to a solution of N-methyl-N-6-(2-methylimidazo[4,5-c]pyridin-1-yl)hexanoyl-L-leucine ethyl ester (200 mg, 0.50 mmol) in ethanol (70 ml). The reaction mixture was stirred at room temperature overnight. The solvent was removed under reduced pressure and water was added to the residue. The pH of the resulting solution was adjusted to pH 6 by the addition of 2M HCl, the mixture was saturated with sodium chloride and extracted with DCM. The combined organic extracts were dried over anhydrous sodium sulphate, filtered and evaporated to give N-methyl-N-6-(2-methylimidazo[4,5-c]pyridin-1-yl)hexanoyl-L-leucine (70 mg, 38%) as a white foam.

i.r. (CDCl$_3$) 2590, 2215, 1720, 1640, 1400, 1315 cm$^{-1}$ delta$_H$ 9.51 (1H, s), 8.40 (1H, d, J 6.4 Hz), 7.89 (1H, d, J 6.4 Hz), 5.18 (1H, dd, J 10.4 Hz, 5.4 Hz), 4.48–4.31 (2H, m), 2.83 (3H, s), 2.75 (3H, s), 2.65–2.18 (2H, m), 1.93–1.30 (9H, m), 0.86 (3H, d, J 6.8 Hz), 0.82 (3H, d, J 6.5 Hz); delta$_C$ (CD$_3$OD) 178.57, 177.27, 167.89, 155.81, 137.08, 130.86, 119.00, 58.23, 40.82, 40.83, 36.40, 34.64, 32.79, 29.67, 28.61, 27.94, 26.09, 24.11.

EXAMPLES 111 and 112

The compounds of Examples 111 and 112 were prepared by the procedure of Example 110 starting from the compounds of Examples 56(C) and 57(A) respectively.

111. N-Methyl-N-6-(2-methylimidazo[4,5-c]pyridin-5-yl)-hexanoyl-L-leucine

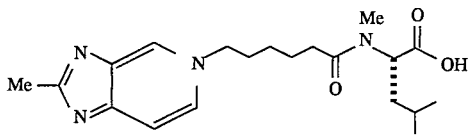

Yellow solid (29% yield): m.p. 80° C. i.r. (CDCl$_3$) 2210, 1720, 1625, 1400, 1125 cm$^{-1}$ delta$_H$ 9.20 (1H, s), 8.50 (1H, d, J 6.5 Hz), 8.00 (1H, d, J 6.7 Hz), 5.05 (1H, dd, J 10.2, 5.2 Hz), 4.80–4.57 (2H, m), 2.91 (3H, s), 2.75 (3H, s), 2.57–2.21 (2H, m), 2.10–1.91 (2H, m), 1.90–1.25 (7H, m), 0.90 (3H, d, J 6.5 Hz), 0.86 (3H, d, J 6.5 Hz); delta$_C$ (CD$_3$OD) 178.29, 166.23, 150.20, 142.98, 140.24, 138.00, 114.99, 64.50, 58.79, 41.18, 36.50, 34.95, 34.77, 29.18, 28.74, 27.79, 26.34, 24.33.

112. N-Methyl-N-6-(2-methylimidazo[4,5-c]pyridin-3-yl)-hexanoyl-L-isoleucine

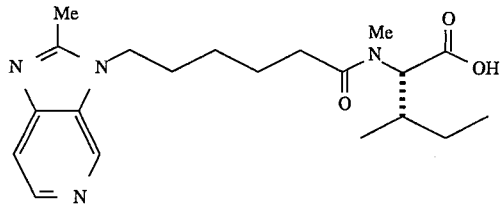

White foam (54% yield after chromatography (silica: 6% methanol and 0.5% acetic acid in DCM): i.r. (CDCl$_3$) 2230, 1715, 1630, 1400, 1135 cm$^{-1}$ delta$_H$ 8.85 (1H, s), 8.37 (1H, d, J 5.3 Hz), 7.67 (1H, d, J 5.5 Hz), 4.97 (1H, t, J 10.3 Hz), 4.20 (2H, t, J 7.2 Hz), 2.97 (3H, s), 2.66 (3H, s), 2.67–2.52 (1H, m), 2.34 (2H, t, J 6.9 Hz), 2.14–1.54 (6H, m), 1.52–1.10 (3H, m), 1.05–0.76 (6H, m); delta$_C$ 173.25, 173.15, 156.57, 148.22, 139.30, 132.66, 130.50, 114.13, 44.38, 33.36, 32.71, 29.57, 26.35, 24.41, 24.12, 15.89, 15.08.

EXAMPLES 113–119

The compounds of Examples 113–119 may be prepared by the hydrolysis of the appropriate amino acid ester derivative according to the method of Example 110.

113. N-6-(2-Methylimidazo[4,5-c]pyridin-1-yl)hexanoyl-L-leucine
114. N-6-(2-Methylimidazo[4,5-c]pyridin-1-yl)hexanoyl-L-phenylalanine
115. N-4-(2-Methylimidazo[4,5-c]pyridin-1-yl)butanoyl-L-leucine
116. N-4-(2-Methylimidazo[4,5-c]pyridin-1-yl)propylsulphonyl-L-methionine
117. N-8-(2-Methylimidazo[4,5-c]pyridin-1-yl)octanoyl-L-leucine
118. N-Methyl-N-8-(2-methylimidazo[4,5-c]pyridin-1-yl)octanoyl-L-leucine
119. N-Methyl-N-11-(2-methylimidazo[4,5-c]pyridin-1-yl)undecanoyl-L-leucine

EXAMPLE 120

N-Methyl-N-4-(2-methylimidazo[4,5-c]pyridin-1-yl)benzoyl-L-leucine ethyl ester

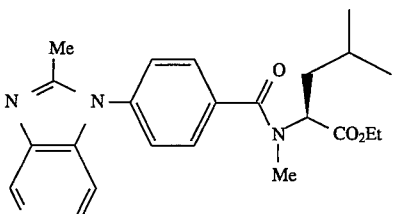

(a) 4-(2-Methylimidazo[4,5-c]-pyridin-1-yl)benzoic acid

Sodium hydroxide (0.39 g, 9.7 mmol) was added to water (5 ml) and the resultant solution added to a stirred solution of 4-(2-methylimidazo[4,5-c]-pyridin- 1-yl)phenylnitrile [Cooper K. et al., J. Med. Chem. 35(17), 3115–3129 (1992)] (224 mg, 0.96 mmol). The mixture was heated under reflux for 1.5 h, cooled, concentrated under reduced pressure and concentrated to dryness to give a brown solid. The residue was taken up in water, neutralised to pH 7 and the resultant mixture passed down an acidic ion exchange column (eluting with 1–30% aqueous ammonia) to give 4-(2-methylimidazo[4,5-c]pyridin-1-yl)benzoic acid (130 mg, 53%) as an amorphous solid.

delta$_H$ (400 MHz) 8.93 (1H, d, J 0.9 Hz), 8.31 (1H, d, J 5.5 Hz), 8.10 (2H, d, J 8.5 Hz), 7.51 (2H, d, J 8.5 Hz), 7.22 (1H, dd, J 5.0, 1.0 Hz), 2.51 (3H, s).

(b) N-4-(2-Methylimidazo[4,5-c]pyridin-1-yl)benzoyl-L-leucine ethyl ester

Oxalyl chloride (200 µl, 2.3 mmol) was added dropwise to a stirred suspension of 4-(2-methylimidazo[4,5-c]-pyridin-1-yl)benzoic acid (130 mg, 0.5 mmol) in dry DCM (10 ml) at 0° C. under argon. DMF (3 drops) was added and the mixture allowed to warm up to ambient temperature slowly. After 1.5 h the reaction mixture was evaporated to dryness under reduced pressure. Dry DCM (10 ml) was added to the residue and L-leucine ethyl ester hydrochloride (142 mg, 0.72 mmol) and triethylamine (280 µl) added to the resulting solution. The mixture was stirred overnight at ambient temperature and concentrated under reduced pressure. The residue was taken up in ethyl acetate and washed with saturated aqueous sodium hydrogen carbonate and brine. The combined organics were dried over anhydrous magnesium sulphate, filtered and concentrated. Column chromatography (silica: 3% methanol in DCM) gave N- 4-(2-methylimidazo[4,5-c]pyridin-1-yl)benzoyl-L-leucine ethyl ester (47 mg, 23%) as a pale yellow oil.

delta$_H$ (400 MHz) 9.06 (1H, s), 8.50 (1H, d, J 5.6 Hz), 8.04 (2H, d, J 8.6 Hz), 7.45 (2H, d, J 8.6 Hz), 7.07 (1H, dd, J 5.6, 1.0 Hz), 6.66 (1H, d, J 8.3 Hz), 4.87 (1H, m), 4.25 (2H, q, J 7.1 Hz), 2.55 (3H, s), 1.85–1.60 (3H, m), 1.32 (3H, t, J 7.1 Hz), 1.03 (3H, d, J 6.1 Hz), 1.00 (3H, d, J 6.3 Hz).

(c) N-Methyl-N-4-(2-methylimidazo[4,5-c]pyridin-1-yl)-benzoyl-L-leucine ethyl ester A solution of N-4-(2-methylimidazo[4,5-c]pyridin-1-yl)-benzoyl-L-leucine ethyl ester (71 mg, 0.18 mmol) in dry THF (3.5 ml) was added via cannula to a stirred suspension of sodium hydride (60% dispersion in oil: 10 mg, 0.25 mmol) in dry THF (1 ml) at room temperature under argon. The mixture was stirred for 0.5 h and dimethyl sulphate (24 µl, 0.25 mmol) added. The mixture was stirred overnight, aqueous ammonium chloride added, the mixture extracted with ethyl acetate and the organics washed with water and brine. The combined organics were dried over anhydrous magnesium sulphate, filtered and concentrated under reduced pressure. Column chromatography (silica: 3% methanol in DCM) gave N-methyl-N-4-(2-methylimidazo [4,5-c]pyridin-1-yl)benzoyl-L-leucine ethyl ester (23 mg, 31%) as a pale yellow oil.

delta$_H$ (400 MHz) 9.06 (1H, s), 8.40 (1H, d, J 5.6 Hz), 8.04 (2H, d, J 7.8 Hz), 7.43 (2H, d, J 8.0 Hz), 7.11 (1H, m), 5.38 (0.6H, m), 4.37 (0.4H, m), 4.24 (2H, br m), 3.03 (1.2H, s), 2.99 (1.8H, s), 2.56 (3H, s), 1.90–1.47 (3H, m), 1.32 (3H, t, J 7.1 Hz), 1.04 (3.6H, d, J 6.3 Hz), 0.89 (1.2H, d, J 5.0 Hz), 0.71 (1.2H, d, J 5.5 Hz).

EXAMPLES 121–129

The compounds of Examples 121–129 may be prepared by the method of Example 120 employing the appropriate amino acid derivative in lieu of L-leucine ethyl ester hydrochloride as starting material.

121. N-Methyl-N-4-(2-methylimidazo[4,5-c]pyridin-1-yl)-benzoyl-L-leucinyl ethyl ether
122. N-Methyl-N-4-(2-methylimidazo[4,5-c]pyridin-1-yl)-benzoyl-L-phenylalanine ethyl ester
123. N-Methyl-N-4-(2-methylimidazo[4,5-c]pyridin-1-yl)-benzoyl-L-leucine n-butyl ester
124. N-Methyl-N-4-(2-methylimidazo[4,5-c]pyridin-1-yl)-benzoyl-L-isoleucine ethyl ester
125. N-Ethyl-N-4-(2-methylimidazo[4,5-c]pyridin-1-yl)-benzoyl-L-leucine ethyl ester
126. N-Methyl-N-4-(2-methylimidazo[4,5-c]pyridin-1-yl)-benzoyl-L-leucine 2-pyridyl amide
127. N-Methyl-N-4-(2-methylimidazo[4,5-c]pyridin-1-yl)-benzoyl-L-leucinyl N'-ethylcarbamate
128. N-Methyl-N-4-(2-methylimidazo[4,5-c]pyridin-1-yl)-benzoyl-L-leucinyl ethanoate
129. N-Methyl-N-4-(2-methylimidazo[4,5-c]pyridin-1-yl)-benzoyl-1-(3-ethyl- 1,2,4-oxadiazol-5-yl)-3-methylbutylamine

EXAMPLE 130

N-Methyl-N-4-(2-(3-pyridyl)ethyl)benzoyl-L-leucine ethyl ester

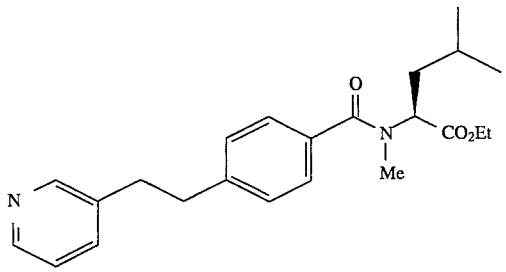

(a) Methyl 4-(2-(3-pyridyl)ethenyl)benzoate

Solid potassium t-butoxide (3.42 g, 30.5 mmol) was added in one portion to a stirred suspension of (3-pyridyl)-methyltriphenylphosphonium chloride hydrochloride (5.20 g, 12.2 mmol) in DMF (90 ml) at 50° C. under argon. After 5 min a solution of methyl 4-formylbenzoate (2.0 g, 12.2 mmol) in DMF (10 ml) was added via cannula. The reaction mixture was stirred overnight at 50° C., and concentrated under reduced pressure. The residue was dissolved in ethyl acetate (250 ml) and washed with water (100 ml). The organics were extracted with 2M HCl (2×100 ml) and the combined acidic aqueous layers washed with ethyl acetate (100 ml) then basified to pH 10 by the addition of aqeous sodium hydroxide followed by potassium carbonate. The mixture was extracted with ethyl acetate (2×200 ml) and the combined organics dried over anhydrous magnesium sulphate, filtered and evaporated to give a 30:70 mixture of trans- and cis-methyl 4-(2-(3-pyridyl)ethenyl)benzoate (2.2 g, 75%) as a brown gum which crystallised on standing.

delta$_H$ (400 MHz) 8.74 (0.3H, d, J 2.0 Hz), 8.51 (0.3H, dd, 4.8, 1.6 Hz), 8.45 (0.7H, d, J 2.2 Hz), 8.42 (0.7H, dd, 4.8, 1.6 Hz), 8.03 (0.6H, d, J 8.4 Hz), 7.90 (1.4H, d, J 8.4 Hz), 7.83 (0.3H, dt, J 8.0, 1.8 Hz), 7.57 (0.6H, d, J 8.5 Hz), 7.46 (0.7H, dt, J 7.9, 1.8 Hz), 7.29 (0.3H, dd, J 7.9, 4.8 Hz), 7.26 (1.4H, d, J 8.2 Hz), 7.17 (0.6H, s), 7.11 (0.7H, dd, J 7.9, 4.7 Hz), 6.75 (0.7H, d, J 12.2 Hz), 6.64 (0.7H, d, J 12.2 Hz), 3.92 (0.9H, s), 3.89 (2.1H, s).

(b) Methyl 4-(2-(3-pyridyl)ethyl)benzoate

Hydrogen gas was slowly bubbled through a vigorously stirred mixture of methyl 4-(2-(3-pyridyl)ethenyl)benzoate (952 mg, 3.98 mmol) and 10% palladium on carbon (95 mg) at room temperature for 4 h. The reaction mixture was filtered through Kieselguhr which was then washed with excess ethyl acetate. The combined organics were evaporated under reduced pressure to give methyl 4-(2-( 3-pyridyl)ethyl)benzoate (900 mg, 94%) as an oil which crystallised on standing.

delta$_H$ (400 MHz) 8.43 (1H, dd, J 4.8, 1.6 Hz), 8.40 (1H, d, J 2.0 Hz), 7.93 (2H, d, J 8.4 Hz), 7.39 (1H, dt, J 7.7, 2.0

Hz), 7.18 (2H, d, J 8.4 Hz), 7.15 (1H, dd, J 7.8, 4.8 Hz), 3.89 (3H, s), 2.95 (4H, m).

(c) N-4-(2-(3-Pyridyl)ethyl)benzoyl-L-leucine ethyl ester

Methyl 4-(2-(3-pyridyl)ethyl)benzoate was dissolved in methanol (10 ml) and a solution of potassium hydroxide (2.1 g, 37.3 mmol) in water (2 ml) added. The mixture was stirred overnight and the pH lowered to ca. 7 by the cautious addition of concentrated hydrochloric acid. Methanol (20 ml) was added and the suspension filtered, the filtrate concentrated to give an oil to which 2M HCl was added to bring the pH to 8. A solid precipitate formed, the solvent was removed under reduced pressure and the residue azeotroped with toluene (1×100 ml, 1×50 ml) to give crude 4-(2-(3-pyridyl)ethyl)benzoic acid. Thionyl chloride (10 ml) and dry DMF (100 µl) were added to the crude 4-(2-(3-pyridyl)ethyl)benzoic acid and the mixture heated under gentle reflux for 1.5 h. The excess thionyl chloride was removed under reduced pressure and the residue azeotroped with toluene (×2) to give crude 4-(2-(3-pyridyl)ethyl)benzoyl chloride hydrochloride as a solid. DCM (20 ml) was added and the resultant suspension treated with L-leucine ethyl ester hydrochloride (733 mg, 3.73 mmol), triethylamine (5.2 ml, 37.3 mmol) and DMAP (30 mg). The mixture was stirred for 1 h at room temperature, diluted with DCM (50 ml) and the solution washed with water (2×20 ml) and saturated brine (20 ml). The combined organics were dried over anhydrous magnesium sulphate, filtered and evaporated to give a yellow oil. Column chromatography (silica: 4% methanol in DCM) gave N-4-(2-(3-pyridyl)ethyl)benzoyl-L-leucine ethyl ester (378 mg, 28%) as a yellow solid.

i.r. (Film) 3355, 2960, 1750, 1635, 1520, 1500, 1160 cm$^{-1}$ delta$_H$ (400 MHz) 8.45 (1H, br d, J 3.7 Hz), 8.42 (1H, br s), 7.71 (2H, d, J 8.3 Hz), 7.43 (1H, dt, J 7.8, 1.9 Hz), 7.21 (1H, dd, J 7.7, 4.9 Hz), 7.18 (2H, d, J 8.3 Hz), 6.49 (1H, d, J 8.3 Hz), 4.83 (1H, m), 4.22 (2H, q, J 7.1 Hz), 2.96 (4H, m), 1.80–1.60 (3H, m), 1.29 (3H, t, J 7.1 Hz), 0.99 (3H, d, J 6.1 Hz), 0.97 (3H, d, J 6.3 Hz).

(d) N-Methyl-N-4-(2-(3-pyridyl)ethyl)benzoyl-L-leucine ethyl ester

A solution of N-4-(2-(3-pyridyl)ethyl)benzoyl-L-leucine ethyl ester (378 mg mg, 1.03 mmol) in dry THF (16 ml) was added via cannula to a stirred suspension of sodium hydride (60% dispersion in oil: 10 mg, 0.25 mmol) in dry THF (3 ml) at room temperature under argon. The mixture was stirred for 0.5 h and dimethyl sulphate (107 µl, 1.13 mmol) added. The mixture was stirred for 1.5 h, saturated aqueous ammonium chloride added (5 ml), the mixture extracted with ethyl acetate (3×20 ml) and the organics washed with brine (10 ml). The combined organics were dried over anhydrous magnesium sulphate, filtered and concentrated under reduced pressure. Column chromatography (silica: 30% hexane in ethyl acetate) gave N-methyl-N-4-(2-(3-pyridyl)-ethyl)benzoyl-L-leucine ethyl ester (21 mg, 7%) as a pale yellow oil.

i.r. (Film) 2960, 1740, 1640, 1395, 1330, 1190 cm$^{-1}$ delta$_H$ (400 MHz) 8.46–8.37 (2H, br m), 7.41 (1H, dt, J 7.7, 1.9 Hz), 7.35–7.08 (5H, br m), 5.34 (0.6H, m), 4.35 (0.4H, m), 4.21 (2H, br m), 3.00–2.82 (7H, m), 1.85–1.40 (3H, m), 1.29 (3H, t, J 7.1 Hz), 0.98 (3.6H, d, J 6.3 Hz), 0.85 (1.2H, d, J 5.0 Hz), 0.62 (1.2H, d, J 5.5 Hz). delta$_C$ (100.6 MHz) 173.37, 166.90, 149.36, 147.50, 147.44, 144.81, 142.60, 136.74, 132.32, 128.82, 127.42, 123.60, 61.53, 51.33, 42.18, 37.24, 34.62, 25.12, 22.93, 22.28, 21.60, 14.27

EXAMPLES 131–139

The compounds of Examples 131–139 may be prepared by the method of Example 130 employing the appropriate amino acid derivative in lieu of L-leucine ethyl ester hydrochloride.

131. N-Methyl-N-4-(2-(3-pyridyl)ethyl)benzoyl-L-leucinyl ethyl ether
132. N-Methyl-N-4-(2-(3-pyridyl)ethyl)benzoyl-L-leucine i-propyl ester
133. N-Ethyl-N-4-(2-(3-pyridyl)ethyl)benzoyl-L-leucine ethyl ester
134. N-Methyl-N-4-(2-(3-pyridyl)ethyl)benzoyl-L-norleucinyl ethyl ether
135. N-Methyl-N-4-(2-(3-pyridyl)ethyl)benzoyl-1-tetrahydrofuryl-3-methylbutylamine
136. N-Methyl-N-4-(2-(3-pyridyl)ethyl)benzoyl-L-valine ethyl ester
137. N-Methyl-N-4-(2-(3-pyridyl)ethyl)benzoyl-N'-methyl-L-tryptophan ethyl ester
138. N-Methyl-N-4-(2-(3-pyridyl)ethyl)benzoyl-O-benzyl-L-serine ethyl ester
139. N-Methyl-N-4-(2-(3-pyridyl)ethyl)benzoyl-L-isoleucinyl ethyl ether

EXAMPLE 140

N-4-(3-Pyridylcyanomethyl)piperazinecarbonyl-L-leucine ethyl ester

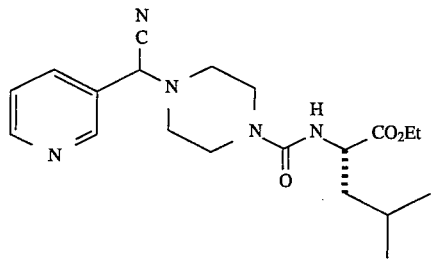

(a) 4-(3-Pyridylcyanomethyl)piperazine

A solution of nicotinaldehyde (5.1 ml, 54 mmol) in methanol (60 ml) was added to a stirred solution of piperazine (14.0 g, 160 mmol) and potassium cyanide (5.4 g, 83 mmol) in water (60 ml) and 1M phosphate buffer solution (pH 7.3: 60 ml). The reaction mixture was stirred for 48 h at ambient temperature and partitioned between water (80 ml) and ethyl acetate (2×100 ml). The organics were dried over anhydrous sodium sulphate, filtered and concentrated. Chromatography (silica gel: 2% methanol in DCM) gave 4-(3-pyridylcyanomethyl)piperazine (1.3 g, 12%) as a colourless oil.

delta$_H$ 8.71 (1H, d, J 2.3 Hz), 8.55 (1H, dd, J 4.8, 1.4 Hz), 7.79 (1H, dt, J 7.8, 2.1 Hz), 7.29 (1H, dd, J 7.7, 4.9 Hz), 4.81 (1H, s), 2.84 (4H, m), 2.48 (4H, m), 1.68 (1H, br s). delta$_C$ 150.03, 149.22, 135.27, 128.74, 123.20, 114.16, 60.44, 50.87, 45.52.

(b) Dipyrid-2-ylcarbonate

Triethylamine (10.5 ml, 75 mmol) was added slowly to a solution of triphosgene (3.0 g, 10 mmol) and 2-hydroxypyridine (5.7 g, 60 mmol) in dry DCM (500 ml) at 0° C. under argon. The mixture was allowed to warm to room temperature and was stirred overnight. The solvent was removed under reduced pressure and the residue taken up in ethyl acetate (500 ml), washed with saturated aqueous sodium hydrogen carbonate (2×150 ml) and brine (200 ml), dried over anhydrous sodium sulphate filtered and concentrated to give an orange oil. Crystallisation from ethyl acetate/hexane gave dipyrid-2-ylcarbonate as an off-white crystalline solid (3.70 g, 57%).

delta$_H$ 8.42 (2H, dd, J 4.8, 1.1 Hz), 7.83 (2H, ddd, J 7.8, 7.7, 1.8 Hz), 7.30–7.23 (4H, m).

(c) N-4-(3-Pyridylcyanomethyl)piperazinecarbonyl-L-leucine ethyl ester

Dipyrid-2-ylcarbonate (234 mg, 1.1 mmol) was added to a stirred solution of triethylamine (100 μl, 1.1 mmol) and 4-(3-pyridylcyanomethyl)piperazine (140 mg, 0.7 mmol) in dry DCM (6 ml) at room temperature under argon. The mixture was stirred overnight, DCM (50 ml) added and the solution washed with saturated aqueous sodium hydrogen carbonate and brine. The organics were dried over anhydrous sodium sulphate, filtered and concentrated to give crude 4-(3-pyridylcyanomethyl)piperazinepyrid-2-ylcarbonate as a colourless oil. Dry DCM (2 ml) was added and the resultant solution transfered via cannula to a stirred mixture of L-leucine ethyl ester hydrochloride (160 mg, 0.8 mmol) and triethylamine (200 μl, 2.2 mmol) in dry DCM (10 ml) at room temperature under argon. The mixture was stirred overnight, DCM (50 ml) added and the solution washed with 10% aqueous citric acid. The organics were concentrated under reduced pressure and the residue partitioned between ethyl acetate and saturated aqueous sodium hydrogen carbonate. The organic phase was washed with brine, dried over anhydrous sodium sulphate, filtered and evaporated to give a yellow foam. Chromatography (silica: 3% methanol in DCM) gave N-4-(3-pyridylcyanomethyl)piperazinecarbonyl-L-leucine ethyl ester (62 mg, 23%) as a colourless oil.

delta$_H$ 8.70 (1H, d, J 2.3 Hz), 8.54 (1H, dd, J 4.8, 1.4 Hz), 7.77 (1H, dt, J 7.8, 2.1 Hz), 7.30 (1H, dd, J 7.7, 4.9 Hz), 4.81 (1H, s), 4.60–4.45 (1H, m), 4.10 (2H, q, J 7.1 Hz), 3.60–3.30 (4H, m), 2.45–2.30 (4H, m), 1.67–1.38 (3H, m), 1.21 (3H, t, J 7.5 Hz), 0.87 (3H, d, J 6.1 Hz), 0.84 (3H, d, J 6.3 Hz).

EXAMPLES 141–143

The compounds of Examples 141–143 may be prepared by the method of Example 140 employing the appropriate amino acid derivative in lieu of L-leucine ethyl ester hydrochloride. The tertiary carbamates may be prepared by alkylation of the corresponding secondary amides or carbamates by the method of Example 130 Step (d).
141. N-4-(3-Pyridylcyanomethyl)piperazinecarbonyl-L-leucine ethyl ester
142. N-Methyl-N-4-(3-pyridylcyanomethyl)piperazinecarbonyl-L-leucine ethyl ester
143. N-Methyl-N-4-(3-pyridylcyanomethyl)piperazinecarbonyl-L-leucinyl ethyl ether

EXAMPLES 144–149

The compounds of Examples 144–149 may be prepared by the method of Example 140 Step (a) employing the appropriate N-alkyl-N-4-piperidinecarbonyl amino acid derivative in lieu of piperazine.
144. N-Methyl-N-4-(3-pyridylcyanomethyl)piperidinecarbonyl-L-leucine ethyl ester
145. N-Methyl-N-4-(3-pyridylcyanomethyl)piperidinecarbonyl-L-leucinyl ethyl ether
146. N-Methyl-N-4-(3-pyridylcyanomethyl)piperidinecarbonyl-L-leucine propyl ester
147. N-Methyl-N-4-(3-pyridylcyanomethyl)piperidinecarbonyl-L-isoleucine ethyl ester
148. N-Methyl-N-4-(3-pyridylcyanomethyl)piperidinecarbonyl-L-phenylalanine ethyl ester
149. N-Ethyl-N-4-(3-pyridylcyanomethyl)piperidinecarbonyl-L-leucinyl ethyl ether

EXAMPLE 150

Inhibition of [$^3$H]-PAF Receptor Binding

The inhibition of [$^3$H]-PAF binding to human platelet plasma membrane by compounds of general formula I was determined by isotopic labelling and filtration techniques. Platelet concentrates were obtained from a hospital blood bank. These platelet concentrates (500–2500 ml.) were centrifuged at 800 rpm for 10 minutes in a SORVALL RC3B centrifuge to remove the red blood cells present. (The word SORVALL is a trade mark.) The supernatant was subsequently centrifuged at 3,000 rpm in a SORVALL RC3B centrifuge to pellet the platelets present. The platelet rich pellets were resuspended in a minimum volume of buffer (150 mM NaCl, 10 mM Tris, 2 mM EDTA, pH 7.5) and layered onto Ficoll-Paque gradients, 9 ml platelet concentrate to 2 ml Ficoll, and centrifuged at 1,900 rpm for 15 minutes in a SORVALL RT6000 centrifuge. This step removes the residual red blood cells and other nonspecific material such as lymphocytes from the preparation. The platelets which form a band between the plasma and the Ficoll were removed, resuspended in the above buffer and centrifuged at 3,000 rpm for 10 minutes in a SORVALL RT6000 centrifuge. The pelleted platelets were resuspended in buffer (10 mM Tris, 5 mM MgCl$_2$, 2 mM EDTA, pH 7.0), snap freezed in liquid N$_2$ and allowed to thaw slowly at room temperature in order to lyse the platelets. The latter step was repeated at least 3 times to ensure proper lysis. The lysed platelets were centrifuged at 3,000 rpm for 10 minutes in a SORVALL RT6000 centrifuge and resuspended in buffer. The latter step was repeated twice in order to remove any cytoplasmic proteins which may hydrolyse the platelet activating factor (PAF) receptor. The prepared platelet membranes may be stored at −70° C. After thawing the prepared membranes were centrifuged in a SORVALL RT6000 at 3,000 rpm for 10 minutes and resuspended in assay buffer.

The assay was conducted by preparing a series of Trisbuffered solutions of the selected antagonist of predetermined concentrations. Each of these solutions contained [$^3$H]-PAF (0.5 nM; 1-O-[$^3$H]octadecyl-2-acetyl-sn-glycero-3-phosphoryl choline with a specific activity of 132 Ci/mmol), unlabelled PAF (1000 nM), a known amount of the test antagonist, and a sufficient amount of Tris-buffer solution (10 mM Tris, 5 mM MgCl$_2$, pH 7.0, 0.25% BSA) to make the final volume 1 ml. Incubation was initiated by the addition of 100 μg of the isolated membrane fraction to each of the above solutions at 0° C. Two control samples, one (C1) which contained all the ingredients described above except the antagonist and the other (C2) contains C1 plus a 1000-fold excess of unlabelled PAF, were also prepared and incubated simultaneously with the test samples. After 1 hour incubation, each solution was filtered rapidly under vacuo through a WHATMAN GF/C glass fibre filter in order to separate unbound PAF from bound PAF. (The word WHATMAN is a trade mark.) The residue in each case was rapidly washed 4 times with 5 ml cold (4° C.) Trisbuffer solution. Each washed residue was dried under vacuum on a sampling manifold and placed into vials containing 20 ml of OPTIPHASE MP scintillation fluid and the radioactivity counted in a liquid scintillation counter. (The word OPTIPHASE is a trade mark.) Defining the counts for total binding with antagonist from a test sample as "TBA"; the counts for total binding from the control sample C1 as "TB"; and the counts for nonspecific binding from the control sample C2 as "NSB", the percent inhibition of each test antagonist can be determined by the following equation:

% Inhibition=[(TB−TBA)/SB]×100 where the specific binding SB=TB−NSB

Table 1 lists results from this assay for inhibition of [$^3$H]-PAF receptor binding for illustrative examples of the compounds of this invention.

TABLE 1

| | Results for inhibition of [³H]-PAF receptor binding |
|---|---|
| Example | Inhibition of [³H]-PAF binding IC$_{50}$ nM |
| 1B | 15 |
| 11B | 3 |
| 98B | 1 |

EXAMPLE 151

Inhibition of PAF-Induced Hypotension in the Rat

The activity of the compounds of general formula I is also demonstrated in vivo by their ability to reverse the hypotension caused by an infusion of PAF in rats. Male Sprague-Dawley rats (300–350 g) were anaesthetised with a mixture of sodium pentobarbitone, 22.5 mg/kg and thiopental 62.5 mg/kg. Through a midline incision in the neck, the trachea was cannulated and the animals breathed spontaneously. A carotid artery was cannulated for the measurement of blood pressure and this signal was used to trigger a rate meter to measure heart rate. Both jugular veins were cannulated: one for the infusion of PAF and the other for the bolus administration of test compounds.

PAF, 100 ng/kg/min was infused i.v. until a sustained fall in mean blood pressure of 50 mmHg was achieved. Test compounds were administered i.v. as a bolus and resulted in a dose dependent reversal of the PAF induced hypotension. The peak of this reversal was measured and the dose to cause a 50% reversal of the hypotensive PAF response (ED$_{50}$) calculated by straight line interpolation and the results are presented in Table 2.

TABLE 2

| Results for inhibition of PAF-induced hypotension in the rat | |
|---|---|
| Example | ED$_{50}$ (µg/kg i.v.) |
| 11B | 30.5 |
| 33B | 1.8 |

What is claimed is:
1. A compound of general formula I:

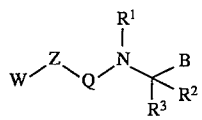

wherein:

W represents imidazo [4,5-c]pyridin-1-yl, imidazo[4,5-c]pyridin-3-yl and imidazo-[4,5-c]pyridin-5-yl any one of which may be substituted with one or more —C$_1$–C$_6$ alkyl substituents;

Z represents:
a) a divalent alkanediyl, alkenediyl or alkynediyl group from 2 to 12 carbon atoms which may be a straight or branched-chain provided that, when Z represents a branched chain at least two carbon atoms separate W from the group Q, wherein the said group is either unsubstituted or substituted by one or more substituents selected from hydroxy, —OC$_1$–C$_6$ alkyl, —SC$_1$–C$_6$ alkyl and halo; or b) a —(CH$_2$)$_q$U(CH$_2$)$_r$— group, optionally substituted by one or more substituents selected from hydroxy, —OC$_1$–C$_6$ alkyl, halo and nitrile, wherein q is an integer from 0–3, r is an integer from 0–3 and U is —O—, or —S—;

Q represents a carbonyl, thiocarbonyl or sulphonyl group;

R$^1$ represents hydrogen, C$_1$–C$_6$ alkyl, C$_2$–C$_6$ alkenyl, C$_2$–C$_6$ alkynyl, COC$_1$–C$_6$ alkyl, —CO$_2$C$_1$–C$_6$ alkyl, —(CO$_2$C$_1$–C$_6$ alkyl)phenyl, —(C$_1$–C$_6$ alkyl)CO$_2$C$_1$–C$_6$ alkyl, —(C$_1$–C$_6$ alkyl)phenyl, —C$_3$–C$_8$ cycloalkyl, —C$_4$–C$_8$ cycloalkenyl or phenyl, which may be optionally substituted by one or more substituents selected from —C$_1$–C$_6$ alkyl,—OC$_1$–C$_6$ alkyl, halogen, —CF$_3$ or —CN;

R$^2$ represents hydrogen, halogen, —C$_1$–C$_6$ alkyl which may be substituted by one or more halogen atoms, —C$_2$–C$_6$ alkenyl, —C$_2$–C$_6$ alkynyl, —(C$_1$–C$_6$ alkyl)CO$_2$C$_1$–C$_6$ alkyl, —(C$_1$–C$_6$ alkyl), SC$_1$–C$_6$ alkyl, —(C$_1$–C$_6$ alkyl),OC$_1$–C$_6$ alkyl, —(C$_1$–C$_6$ alkyl)N(C$_1$–C$_6$ alkyl)$_2$, —C$_3$–C$_8$ cycloalkyl, —C$_4$–C$_8$ cycloalkenyl, —(C$_1$–C$_6$ alkyl)C$_3$–C$_8$ cycloalkyl, —(C$_1$–C$_6$ alkyl)C$_4$–C$_8$ cycloalkenyl, —(C$_1$–C$_6$ alkyl)OC$_3$–C$_8$ cycloalkyl, —(C$_1$–C$_6$ alkyl)OC$_4$–C$_8$ cycloalkenyl, —(C$_1$–C$_6$ alkyl)SC$_3$–C$_8$ cycloalkyl, —(C$_1$–C$_6$ alkyl)SC$_4$–C$_8$ cycloalkenyl, a side chain of a naturally occurring amino acid, a group —D or —(C$_1$–C$_6$ alkyl)OD wherein D is a group

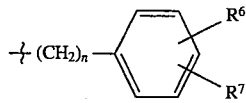

wherein n is an integer from 0 to 3, and
each of R$^6$ and R$^7$ is independently hydrogen, —C$_1$–C$_6$ alkyl, —C$_2$–C$_6$ alkenyl, —C$_2$–C$_6$ alkynyl, halogen, —CN, —CO$_2$H, —CO$_2$C$_1$–C$_6$ alkyl, —CONH$_2$, —CONHC$_1$–C$_6$ alkyl, —CON(C$_1$–C$_6$ alkyl)$_2$, —CHO, —CH$_2$OH, —CF$_3$, —OC$_1$–C$_6$ alkyl, —SC$_1$–C$_6$ alkyl, —SOC$_1$–C$_6$ alkyl, —SO$_2$C$_1$–C$_6$ alkyl, —NH$_2$ or —NHCOMe;

(except when q=0 and Q is carbonyl) R$^1$ together with R$^2$ and the atoms to which they are attached form a 5 to 8 membered nitrogen-containing heterocyclic ring;

R$^3$ represents hydrogen or halogen;

B represents:
a) a —VR$^8$ group wherein V is —C(=O)O— or —CH$_2$O—; and

R$^8$ is hydrogen, —C$_1$–C$_{18}$ alkyl, —C$_2$–C$_{18}$ alkenyl, —C$_2$–C$_{18}$ alkynyl, —(C$_1$–C$_6$ alkyl)OC$_1$–C$_6$ alkyl, —(C$_1$–C$_6$ alkyl)SC$_1$–C$_6$ alkyl, —(C$_1$–C$_6$ alkyl)O(C$_1$–C$_6$ alkyl)OC$_1$–C$_6$ alkyl, —C$_3$–C$_8$ cycloalkyl, —C$_4$–C$_8$ cycloalkenyl or pyridyl, (any of which may optionally be substituted with one or more substituents selected from halogen, hydroxyl, nitro, nitrile or carboxyl), —C$_1$–C$_4$ perfluoroalkyl, a group —D as defined above or a —(C$_1$–C$_6$ alkyl)OD group wherein D is as defined above;
or a pharmaceutically or veterinarily acceptable acid addition salt or hydrate thereof.

2. A compound as claimed in claim 1 wherein W represents 2-methylbenzimidazol- 1-yl, 2-methylimidazo[4,5-c]pyridin-1-yl, 2-methylimidazo[4,5-c]pyridin-3-yl and 2-methylimidazo[4,5-c]pyridin-5-yl.

3. A compound as claimed in claim 2, wherein Z represents:
a) an alkanediyl having from 3 to 11 carbon atoms group, an alkenediyl group or an alkynediyl group, or;

b) a —(CH$_2$)$_q$U(CH$_2$)$_r$— group, optionally substituted by nitrile, wherein
U represents —O— or —S—;
q represents an integer of 0, 1, or 2; and
r represents an integer of 0.

4. A compound as claimed in claim 3, wherein Z represents a propylene, 2-hydroxypropylene, 1-methylpropylene, 1,1-dimethylpropylene, butylene, 1-methylbutylene, 1,1-dimethylbutylene, 3-hydroxybutylene, pentylene, 1-methylpentylene, 1,1-dimethylpentylene, 4-hydroxypentylene, 4-methoxypentylene, hexylene, 1,1-dimethylhexylene, heptylene, 1-methylheptylene, 1,1-dimethylheptylene, octylene, 1,1-dimethyloctylene nonylene, decylene, or undecylene.

5. A compound as claimed in claim 1, wherein Q represents a carbonyl or sulphonyl group.

6. A compound as claimed in claim 1, wherein R$^1$ represents a hydrogen atom, a —C$_1$–C$_6$ alkyl group, a —C$_2$–C$_6$ alkenyl group, or a —(C$_1$–C$_6$ alkyl)CO$_2$C$_1$–C$_6$ alkyl group.

7. A compound as claimed in claim 1, wherein R$^2$ represents a —C$_1$–C$_6$ alkyl group, a —C$_2$–C$_6$ alkenyl group, a —(C$_1$–C$_6$ alkyl)SC$_1$–C$_6$ alkyl group, the side chain of a naturally occurring amino acid, a group —D or a —(C$_1$–C$_6$ alkyl)OD group;

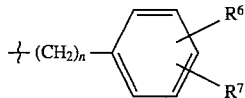

wherein n represents an integer of 0 or 1, R$^6$ represents a hydrogen atom or a —OC$_1$–C$_6$ alkyl group and R$^7$ represents a hydrogen atom.

8. A compound as claimed in claim 7, wherein R$^2$ represents the side chain of the amino acid leucine.

9. A compound as claimed in claim 1, wherein R$^3$ represents a hydrogen atom.

10. N-6-(2-Methylimidazo[4,5-c]pyridin-3-yl)hexanoyl-L-leucine ethyl ester,
N-6-(2-Methylimidazo[4,5-c]pyridin-1-yl)hexanoyl-L-leucine ethyl ester,
N-6-(2-Methylimidazo[4,5-c]pyridin-1-yl)hexanoyl-D-leucine ethyl ester,
N-6-(2-Methylimidazo[4,5-c]pyridin-1-yl)hexanoyl-L-phenylalanine ethyl ester,
N-6-(2-Methylimidazo[4,5-c]pyridin-1-yl)hexanoyl-L-leucine propyl ester,
N-6-(2-Methylimidazo[4,5-c]pyridin-1-yl)hexanoyl-L-norleucine ethyl ester,
N-6-(2-Methylimidazo[4,5-c]pyridin-1-yl)hexanoyl-O-benzyl-L-serine methyl ester,
N-6-(2-Methylimidazo[4,5-c]pyridin-1-yl)-2-methylhexanoyl-L-leucine ethyl ester,
N-6-(2-Methylimidazo[4,5-c]pyridin-1-yl)-2,2-dimethylhexanoyl-L-leucine ethyl ester,
N-6-(2-Methylimidazo[4,5-c]pyridin-1-yl)-5-hydroxyhexanoyl-L-leucine ethyl ester,
N-6-(2-Methylimidazo[4,5-c]pyridin-1-yl)hexanoyl-L-leucine hexadecyl ester,
N-4-(2-Methylimidazo[4,5-c]pyridin-3-yl)butanoyl-L-leucine ethyl ester,
N-4-(2-Methylimidazo[4,5-c]pyridin-1-yl)butanoyl-L-leucine ethyl ester,
N-4-(2-Methylimidazo[4,5-c]pyridin-5-yl)butanoyl-L-leucine ethyl ester,
N-4-(2-Methylimidazo[4,5-c]pyridin-1-yl)butanoyl-L-leucine methyl ester,
N-4-(2-Methylimidazo[4,5-c]pyridin-1-yl)butanoyl-O-methyl-L-tyrosine ethyl ester,
N-4-(2-Methylimidazo[4,5-c]pyridin-1-yl)butanoyl-L-methionine ethyl ester,
N-4-(2-Methylimidazo[4,5-c]pyridin-1-yl)butanoyl-L-norleucine n-butyl ester,
N-4-(2-Methylimidazo[4,5-c]pyridin-1-yl)-2,2-dimethylbutanoyl-L-leucine ethyl ester,
N-4-(2-Methylimidazo[4,5-c]pyridin-1-yl)-3-hydroxybutanoyl-L-leucine ethyl ester,
N-4-(2-Methylimidazo[4,5-c]pyridin-1-yl)butanoyl-L-valine ethyl ester,
N-4-(2-Methylimidazo[4,5-c]pyridin-1-yl)butanoyl-L-leucine hexyl ester,
N-4-(2-Methylimidazo[4,5-c]pyridin-1-yl)butanoyl-L-leucine decyl ester,
N-4-(2-Methylimidazo[4,5-c]pyridin-1-yl)propylsulphonyl-L-alanine ethyl ester,
N-4-(2-Methylimidazo[4,5-c]pyridin-1-yl)propylsulphonyl-L-isoleucine ethyl ester,
N-4-(2-Methylimidazo[4,5-c]pyridin-1-yl)propylsulphonyl-L-norleucine ethyl ester,
N-4-(2-Methylimidazo[4,5-c]pyridin-1-yl)propylsulphonyl-L-methionine ethyl ester,
N-4-(2-Methylimidazo[4,5-c]pyridin-1-yl)propylsulphonyl-L-leucine i-propyl ester,
N-4-(2-Methylimidazo[4,5-c]pyridin-1-yl)propylsulphonyl-L-leucine pentyl ester,
N-4-(2-Methylimidazo[4,5-c]pyridin-1-yl)propylsulphonyl-L-leucine octyl ester,
N-4-(2-Methylimidazo[4,5-c]pyridin-1-yl)propylsulphonyl-L-leucine dodecyl ester,
N-4-(2-Methylimidazo[4,5-c]pyridin-1-yl)propylsulphonyl-L-leucine pentadecyl ester,
N-4-(2-Methylimidazo[4,5-c]pyridin-1-yl)propylsulphonyl-L-leucine hexadecyl ester,
N-4-(2-Methylimidazo[4,5-c]pyridin-1-yl)propylsulphonyl-L-leucine octadecyl ester,
N-4-(2-Methylimidazo[4,5-c]pyridin-3-yl)propylsulphonyl-L-leucinyl ethyl ether,
N-4-(2-Methylimidazo[4,5-c]pyridin-1-yl)propylsulphonyl-L-leucinyl ethyl ether,
N-4-(2-Methylimidazo[4,5-c]pyridin-5-yl)propylsulphonyl-L-leucinyl ethyl ether,
N-4-(2-Methylimidazo[4,5-c]pyridin-1-yl)propylsulphonyl-L-leucinyl methyl ether,
N-4-(2-Methylimidazo[4,5-c]pyridin-1-yl)propylsulphonyl-L-leucinyl octyl ether,
N-4-(2-Methylimidazo[4,5-c]pyridin-1-yl)propylsulphonyl-L-leucinyl hexadecyl ether,
N-4-(2-Methylimidazo[4,5-c]pyridin-1-yl)propylsulphonyl-L-leucinyl benzyl ether,
N-4-(2-Methylimidazo[4,5-c]pyridin-1-yl)propylsulphonyl-L-leucinyl propionate,
N-4-(2-Methylimidazo[4,5-c]pyridin-1-yl)propylsulphonyl-L-leucinyl octadecanoate,
N-5-(2-Methylimidazo[4,5-c]pyridin-3-yl)pentanoyl-L-leucine ethyl ester,
N-5-(2-Methylimidazo[4,5-c]pyridin-1-yl)pentanoyl-L-leucine ethyl ester,
N-5-(2-Methylimidazo[4,5-c]pyridin-1-yl)pentanoyl-L-leucine i-propyl ester,
N-5-(2-Methylimidazo[4,5-c]pyridin-1-yl)pentanoyl-O-methyl-L-tyrosine ethyl ester,
N-5-(2-Methylimidazo[4,5-c]pyridin-1-yl)pentanoyl-D,L-allylglycine ethyl ester,
N-5-(2-Methylimidazo[4,5-c]pyridin-1-yl)pentanoyl-L-norleucine allyl ester,
N-5-(2-Methylimidazo[4,5-c]pyridin-1-yl)-2-methylpentanoyl-L-leucinyl ethyl ether,
N-5-(2-Methylimidazo[4,5-c]pyridin-1-yl)-2,2-dimethylpentanoyl-L-leucine 2-benzoxyethylethyl ester, N-5-(2-Methylimidazo[4,5-c]pyridin-1-yl)-3-hydroxypentanoyl-L-leucine 2-(2-ethoxyethoxy)ethyl ester,
N-Methyl-N-6-(2-methylimidazo[4,5-c]pyridin-3-yl)hexanoyl-L-leucine ethyl ester,
N-Methyl-N-6-(2-methylimidazo[4,5-c]pyridin-1-yl)hexanoyl-L-leucine ethyl ester,
N-Methyl-N-6-(2-methylimidazo[4,5-c]pyridin-5-yl)hexanoyl-L-leucine ethyl ester,
N-Methyl-N-6-(2-methylimidazo[4,5-c]pyridin-3-yl)hexanoyl-L-isoleucine allyl ester,
N-Methyl-N-6-(2-methylimidazo[4,5-c]pyridin-1-yl)hexanoyl-L-isoleucine allyl ester,
N-Methyl-N-6-(2-methylimidazo[4,5-c]pyridin-5-yl)hexanoyl-L-isoleucine allyl ester,
N-Methyl-N-6-(2-methylimidazo[4,5-c]pyridin-3-yl)hexanoyl-L-leucinyl ethyl ether,
N-Methyl-N-6-(2-methylimidazo[4,5-c]pyridin-1-yl)hexanoyl-L-leucinyl ethyl ether,
N-Methyl-N-6-(2-methylimidazo[4,5-c]pyridin-5-yl)hexanoyl-L-leucinyl ethyl ether,
N-Methyl-N-6-(2-methylimidazo[4,5-c]pyridin-1-yl)hexanoyl-L-leucinyl hexadecyl ether,
N-Methyl-N-6-(2-methylimidazo[4,5-c]pyridin-1-yl)hexanoyl-L-phenyl-alaninyl ethyl ether,
N-Methyl-N-6-(2-methylimidazo[4,5-c]pyridin-1-yl)hexanoyl-L-leucinyl 4-methoxybenzyl ether,
N-Methyl-N-6-(2-methylimidazo[4,5-c]pyridin-1-yl)hexanoyl-L-norleucinyl ethyl ether,
N-Methyl-N-6-(2-methylimidazo[4,5-c]pyridin-1-yl)hexanoyl-O-benzyl-L-serinyl ethyl ether,
N-Methyl-N-6-(2-methylimidazo[4,5-c]pyridin-1-yl)-2-methylhexanoyl-L-leucinyl ethyl ether,
N-Ethoxycarbonyl-N-6-(2-methylimidazo[4,5-c]pyridin-1-yl)hexanoyl-L-leucinyl ethyl ether,
N-Methyl-N-6-(2-methylimidazo[4,5-c]pyridin-1-yl)-5-methoxyhexanoyl-L-leucinyl ethyl ether,
N-Methyl-N-4-(2-methylimidazo[4,5-c]pyridin-1-yl)butanoyl-L-leucine ethyl ester,
N-Allyl-N-4-(2-methylimidazo[4,5-c]pyridin-1-yl)butanoyl-L-leucine i-propyl ester,
N-Methyl-N-4-(2-methylimidazo[4,5-c]pyridin-1-yl)butanoyl-L-leucinyl ethyl ether,
N-Methyl-N-4-(2-methylimidazo[4,5-c]pyridin-1-yl)-2-methylbutanoyl-L-leucinyl ethyl ether,
N-Methyl-N-5-(2-methylimidazo[4,5-c]pyridin-1-yl)pentanoyl-L-leucine ethyl ester,
N-Methyl-N-5-(2-methylimidazo[4,5-c]pyridin-1-yl)pentanoyl-L-leucinyl ethyl ether,
N-Methyl-N-5-(2-methylimidazo[4,5-c]pyridin-1-yl)-2-methylpentanoyl-L-leucinyl ethyl ether,
N-Methyl-N-5-(2-methylimidazo[4,5-c]pyridin-1-yl)pentanoyl-L-leucinyl hexadecyl ether,
N-Methyl-N-3-(2-methylimidazo[4,5-c]pyridin-1-yl)propylsulphonyl-L-leucine ethyl ester,
N-Methyl-N-3-(2-methylimidazo[4,5-c]pyridin-1-yl)propylsulphonyl-L-leucine i-propyl ester,
N-Methyl-N-3-(2-methylimidazo[4,5-c]pyridin-1-yl)propylsulphonyl-L-leucinyl ethyl ether,
N-Methyl-N-3-(2-methylimidazo[4,5-c]pyridin-1-yl)propylsulphonyl-L-leucinyl hexadecyl ester,
N-Methyl-N-4-(2-methylimidazo[4,5-c]pyridin-1-yl)butylsulphonyl-L-leucine ethyl ester,
N-Methyl-N-4-(2-methylimidazo[4,5-c]pyridin-1-yl)butylsulphonyl-L-leucinyl ethyl ether,
N-Methyl-N-4-(2-methylimidazo[4,5-c]pyridin-1-yl)butylsulphonyl-L-leucinyl heptadecyl ether,
N-Methyl-N-5-(2-methylimidazo[4,5-c]pyridin-1-yl)pentylsulphonyl-L-leucine ethyl ester,
N-Methyl-N-5-(2-methylimidazo[4,5-c]pyridin-1-yl)pentylsulphonyl-L-leucine i-propyl ester,
N-Methyl-N-5-(2-methylimidazo[4,5-c]pyridin-1-yl)pentylsulphonyl-L-leucinyl ethyl ether,
N-8-(2-Methylimidazo[4,5-c]pyridin-3-yl)octanoyl-L-leucine ethyl ester,
N-8-(2-Methylimidazo[4,5-c]pyridin-1-yl)octanoyl-L-leucine ethyl ester,
N-8-(2-Methylimidazo[4,5-c]pyridin-5-yl)octanoyl-L-leucine ethyl ester,
N-8-(2-Methylimidazo[4,5-c]pyridin-1-yl)-2-methyloctanoyl-L-leucine ethyl ester,
N-8-(2-Methylimidazo[4,5-c]pyridin-1-yl)-2,2-dimethyloctanoyl-L-phenylalanine ethyl ester,
N-Methyl-N-8-(2-methylimidazo[4,5-c]pyridin-1-yl)octanoyl-L-leucine i-propyl ester,
N-Methyl-N-8-(2-methylimidazo[4,5-c]pyridin-1-yl)octanoyl-L-leucinyl ethyl ether,
N-Methyl-N-8-(2-methylimidazo[4,5-c]pyridin-1-yl)octanoyl-1-(3-ethyl- 1,2,4-oxadiazol-5-yl)-3-methylbutylamine,
N-7-(2-Methylimidazo[4,5-c]pyridin-1-yl)heptanoyl-L-leucine ethyl ester,
N-Methyl-N-7-(2-methylimidazo[4,5-c]pyridin-1-yl)heptanoyl-L-leucinyl ethyl ether,
N-Methyl-N-7-(2-methylimidazo[4,5-c]pyridin-1-yl)-2,2-dimethyl-heptanoyl-L-leucinyl ethyl ether,
N-11-(2-Methylimidazo[4,5-c]pyridin-3-yl)undecanoyl-L-leucine ethyl ester,
N-11-(2-Methylimidazo[4,5-c]pyridin-1-yl)undecanoyl-L-leucine ethyl ester,
N-9-(2-Methylimidazo[4,5-c]pyridin-1-yl)nonanoyl-L-leucine ethyl ester,
N-Methyl-N-9-(2-methylimidazo[4,5-c]pyridin-1-yl)-nonanoyl-L-leucine i-propyl ester,
N-Methyl-N-9-(2-methylimidazo[4,5-c]pyridin-1-yl)-nonanoyl-L-leucinyl ethyl ether,
N-Methyl-N-9-(2-methylimidazo[4,5-c]pyridin-1-yl)-2,2-dimethylnonanoyl-L-leucinyl ethyl ether,
N-Methyl-N-10-(2-methylimidazo[4,5-c]pyridin-1-yl)decanoyl-L-leucinyl ethyl ester,
N-Methyl-N-10-(2-methylimidazo[4,5-c]pyridin-1-yl)decanoyl-L-leucine ethyl ester,
N-Methyl-N-11-(2-methylimidazo[4,5-c]pyridin-1-yl)undecanoyl-L-leucine ethyl ester,
N-Methyl-N-11-(2-methylimidazo[4,5-c]pyridin-1-yl)undecanoyl-L-leucinyl ethyl ether,
N-Methyl-N-12-(2-methylimidazo[4,5-c]pyridin-1-yl)dodecanoyl-L-leucinyl ethyl ether,
N-Methyl-N-6-(2-methylimidazo[4,5-c]pyridin-1-yl)hexanoyl-D-leucine ethyl ester,
N-Methyl-N-6-(2-methylimidazo[4,5-c]pyridin-1-yl)hexanoyl-L-phenylalanine ethyl ester,
N-Methyl-N-4-(2-methylimidazo[4,5-c]pyridin-1-yl)benzoyl-L-leucine ethyl ester,
N-Methyl-N-4-(2-methylimidazo[4,5-c]pyridin-1-yl)benzoyl-L-leucinyl ethyl ether,
N-Methyl-N-4-(2-methylimidazo[4,5-c]pyridin-1-yl)benzoyl-L-phenylalanine ethyl ester,
N-Methyl-N-4-(2-methylimidazo[4,5-c]pyridin-1-yl)benzoyl-L-leucine n-butyl ester,
N-Methyl-N-4-(2-methylimidazo[4,5-c]pyridin-1-yl)benzoyl-L-isoleucine ethyl ester,
N-Ethyl-N-4-(2-methylimidazo[4,5-c]pyridin-1-yl)benzoyl-L-leucine ethyl ester,
or a salt of any of the above compounds.

* * * * *